(12) United States Patent
McBride et al.

(10) Patent No.: US 9,199,032 B2
(45) Date of Patent: *Dec. 1, 2015

(54) SYSTEM AND KIT FOR DELIVERING COLLAGEN BIOGLASS COMPOSITE BONE GRAFTING MATERIALS FOR REGENERATING HARD TISSUES

(71) Applicant: NOVABONE PRODUCTS, LLC, Alachua, FL (US)

(72) Inventors: Dennis McBride, Lebanon, NJ (US); Joshua P. Clark, Alachua, FL (US); Richard Davis, St. Augustine, FL (US); Gregory J. Pomrink, Newberry, FL (US); Zehra Tosun, Gainesville, FL (US); David C. Greenspan, Gainesville, FL (US)

(73) Assignee: NOVABONE PRODUCTS, LLC, Alachua, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/572,349

(22) Filed: Dec. 16, 2014

(65) Prior Publication Data

US 2015/0105748 A1 Apr. 16, 2015

Related U.S. Application Data

(63) Continuation-in-part of application No. 14/227,886, filed on Mar. 27, 2014, which is a continuation-in-part of application No. 13/833,400, filed on Mar. 15, 2013, now Pat. No. 9,144,629, which is a continuation-in-part of application No. 13/039,627, filed on Mar. 3, 2011, now Pat. No. 8,795,702.

(60) Provisional application No. 61/710,332, filed on Oct. 5, 2012, provisional application No. 61/310,129, filed on Mar. 3, 2010.

(51) Int. Cl.
| | | |
|---|---|---|
| *A61M 5/145* | (2006.01) | |
| *A61K 33/42* | (2006.01) | |
| *A61K 38/39* | (2006.01) | |
| *A61K 45/06* | (2006.01) | |
| *A61L 27/10* | (2006.01) | |
| *A61L 27/24* | (2006.01) | |
| *A61L 27/46* | (2006.01) | |
| *A61L 27/56* | (2006.01) | |
| *A61L 27/44* | (2006.01) | |

(52) U.S. Cl.
CPC ............. *A61M 5/1452* (2013.01); *A61L 27/10* (2013.01); *A61L 27/24* (2013.01); *A61L 27/446* (2013.01); *A61L 27/46* (2013.01); *A61L 27/56* (2013.01); *A61L 2430/02* (2013.01)

(58) Field of Classification Search
CPC ..... A61L 27/46; A61L 2430/02; A61L 27/24; A61L 27/56; A61L 27/3633; A61L 27/365; A61L 27/446; A61L 27/025; A61K 33/42; A61K 38/39; A61K 45/06; C08L 89/06; A61M 5/1452

See application file for complete search history.

(56) References Cited

U.S. PATENT DOCUMENTS

| | | | |
|---|---|---|---|
| 4,851,046 | A | 7/1989 | Low et al. |
| 5,320,844 | A | 6/1994 | Liu |
| 5,912,225 | A | 6/1999 | Mao et al. |
| 5,977,204 | A | 11/1999 | Boyan et al. |
| 6,027,742 | A | 2/2000 | Lee et al. |
| 6,045,555 | A | 4/2000 | Smith et al. |
| 6,153,212 | A | 11/2000 | Mao et al. |
| 6,166,173 | A | 12/2000 | Mao et al. |
| 6,187,047 | B1 | 2/2001 | Kwan et al. |
| 6,224,913 | B1 | 5/2001 | Ducheyne et al. |
| 6,238,687 | B1 | 5/2001 | Mao et al. |
| 6,322,797 | B1 | 11/2001 | Mao et al. |
| 6,328,990 | B1 | 12/2001 | Ducheyne et al. |
| 6,344,496 | B1 | 2/2002 | Niederauer et al. |
| 6,395,036 | B1 | 5/2002 | Czernuszka et al. |
| 6,413,538 | B1 | 7/2002 | Garcia et al. |
| 6,417,166 | B2 | 7/2002 | Liu |
| 6,569,466 | B2 | 5/2003 | Ducheyne et al. |
| 6,709,744 | B1 * | 3/2004 | Day et al. ............ 428/403 |
| 6,764,517 | B2 | 7/2004 | Yamamoto et al. |
| 6,902,584 | B2 | 6/2005 | Kwan et al. |
| 6,949,251 | B2 | 9/2005 | Dalai et al. |
| 6,969,501 | B2 | 11/2005 | Sapieszko et al. |
| 6,991,802 | B1 | 1/2006 | Ahola et al. |
| 6,991,803 | B2 | 1/2006 | Sapieszko et al. |
| 7,014,640 | B2 | 3/2006 | Kemppainen et al. |

(Continued)

FOREIGN PATENT DOCUMENTS

| | | |
|---|---|---|
| WO | WO98/46164 | 10/1998 |
| WO | WO2013/188336 A2 | 12/2013 |

OTHER PUBLICATIONS

Hench, et al., "Bonding Mechanisms at the Interface of Ceramic Prosthetic Materials," *J. Biomed. Mater. Res. Symposium*, 2(1):117-141 (1971).

(Continued)

*Primary Examiner* — Abigail Fisher
(74) *Attorney, Agent, or Firm* — Brinks Gilson & Lione

(57) ABSTRACT

Methods for producing a composite bone graft material that can regenerate bony defects in the body are provided. Also, methods, kits and delivery systems for a minimally invasive delivery of a composition for regenerating bone at or near the site of a bony defect that include, the composition for regenerating bone comprising collagen and bioactive glass are provided.

44 Claims, 11 Drawing Sheets

(56) References Cited

U.S. PATENT DOCUMENTS

| | | | |
|---|---|---|---|
| 7,156,880 | B2 | 1/2007 | Evans et al. |
| 7,166,133 | B2 | 1/2007 | Evans et al. |
| 7,189,263 | B2 | 3/2007 | Erbe et al. |
| 7,229,971 | B2 | 6/2007 | Tanaka et al. |
| 7,241,459 | B2 | 7/2007 | Fechner et al. |
| 7,531,004 | B2 | 5/2009 | Bagga et al. |
| 7,534,451 | B2 | 5/2009 | Erbe et al. |
| 7,544,212 | B2 | 6/2009 | Li et al. |
| 7,544,496 | B2 | 6/2009 | Gower et al. |
| 7,547,499 | B2 | 6/2009 | Veregin et al. |
| 7,578,845 | B2 | 8/2009 | Nies et al. |
| 7,621,963 | B2 | 11/2009 | Simon et al. |
| 8,252,055 | B2 | 8/2012 | McKay |
| 8,795,702 | B2 * | 8/2014 | Greenspan et al. ........... 424/422 |
| 2002/0055143 | A1 | 5/2002 | Bell et al. |
| 2002/0112981 | A1 * | 8/2002 | Cooper et al. ................ 206/438 |
| 2004/0009598 | A1 | 1/2004 | Hench et al. |
| 2005/0251149 | A1 * | 11/2005 | Wenz .............................. 606/94 |
| 2005/0251267 | A1 | 11/2005 | Winterbottom |
| 2008/0187571 | A1 * | 8/2008 | Clineff et al. ................. 424/426 |
| 2008/0221701 | A1 * | 9/2008 | Zhong et al. ............... 623/23.62 |
| 2010/0312355 | A1 | 12/2010 | Yahav et al. |
| 2011/0217388 | A1 | 9/2011 | Greenspan et al. |
| 2012/0035741 | A1 | 2/2012 | Li et al. |
| 2013/0330410 | A1 | 12/2013 | Pomrink et al. |
| 2013/0331898 | A1 | 12/2013 | Nyemscek et al. |
| 2014/0017281 | A1 | 1/2014 | Pomrink et al. |
| 2014/0079789 | A1 | 3/2014 | Pomrink et al. |

OTHER PUBLICATIONS

Piotrowski, et al., "Mechanical Studies of the Bone Bioglass Interfacial Bond," *J. Biomed. Mater. Res. Symposium*, 6:47-61 (1975).

Wilson, et al., "Toxicology and biocompatibility of biolgasses," *J. of Biomed. Materials Research*, 15:805-817 (1981).

Pereira, et al., "Bioactive glass and hybrid scaffolds prepared by sol-gel method for bone tissue engineering," *Advances in Applied Ceramics*, 104(1):35-42 (2005).

Chen, et al., "A new sol-gel process for producing $Na_2O$-containing bioactive glass ceramics," *Acta Biomaterialia*, 6:4143-4153 (2010).

International Search Report completed Apr. 14, 2011 in International Application No. PCT/US2011/026961, filed Mar. 3, 2011.

English language translation of the International Preliminary Report on Patentability dated Sep. 4, 2012, from corresponding International Application No. PCT/US2011/026961, filed Mar. 3, 2011.

European Search Report received in Application No. 11751335.8 dated Jul. 7, 2014.

International Search Report received in PCT Application No. PCT/US14/32035 dated Aug. 20, 2014.

Li et al., "Thermoreversible Micellization and Gelation of a Blend of Pluronic Polymers," *Polymer*, 49:1952-1960 (2008).

Lenaerts et al., "Temperature-Dependent Rheological Behavior of Pluronic F-127 Aqueous Solutions," *Intl. J. of Pharm.*, 39:121-127 (1987).

Ivanova et al., "Effect of Pharmaceutically Acceptable Glycols on the Stability of Liquid Crystalline Gels Formed by Poloxamer 407 in Water," *Journal of Colloid and Interface Science*, 252:226-235 (2002).

Taylor & Francis, Ltd., "Safety Assessment of Poloxamers 101, 105, 108, 122, 123, 124, 181, 182, 183, 184, 185, 188, 212, 215, 217, 231, 234, 235, 237, 238, 282, 284, 288, 331, 333, 334, 335, 338, 401, 402, 403, and 407, Poloxamer 105 Benzoate, and Poloxamer 182 Dibenzoate and Uses in Cosmetics," *Intl. J. of Toxicology*, 27(2):93-128 (2008).

Patel et al., "Poloxamers: A Pharmaceutical Excipients with Therapeutic Behaviors," *Intl. J. of PharmTech Research*, 1(2):299-303 (2009).

Rey-Rico et al., "Osteogenic Efficiency of in Situ Gelling Poloxamine Systems With and Without Bone Morphogenetic Protein-2," *European Cells and Materials*, 21:317-340 (2011).

Verne et al., "Surface Functionalization of Bioactive Glasses," *J. Biomed. Mater. Res. A.*, 90(A):981-992 (2009).

International Search Report and Written Opinion received in PCT Application No. PCT/US14/70633 dated Mar. 25, 2015.

* cited by examiner

SYSTEM AND KIT FOR DELIVERING COLLAGEN BIOGLASS COMPOSITE BONE GRAFTING MATERIALS FOR REGENERATING HARD TISSUES

RELATED APPLICATIONS

This application is a continuation-in-part application of U.S. application Ser. No. 14/227,886, filed Mar. 27, 2014, which is a continuation-in-part of U.S. application Ser. No. 13/833,400, filed Mar. 15, 2013, which claims priority under 35 U.S.C. §119 to U.S. Provisional Application No. 61/710,332, filed Oct. 5, 2012, and which is also a continuation-in-part of U.S. application Ser. No. 13/039,627, filed Mar. 3, 2011, which claims benefit of U.S. Provisional Application No. 61/310,129, filed Mar. 3, 2010, the entire contents of which are hereby incorporated herein by reference.

BACKGROUND

There are dozens of materials used today for the repair and regeneration of bony defects. Bone is composite material that is comprised of collagen, cells, a form of calcium hydroxyapatite crystals and small quantities of other proteins and organic molecules. The chemistry and physical nature of this composite affords it unique properties of high strength, rigidity, and an ability to adapt to changing loads in the body. However, when injuries to bone occur it is sometimes necessary to find a way to fill voids or gaps, and to encourage the repair and regeneration of the bone tissue.

Autograft bone, usually taken from the iliac crest remains the gold standard for filling bony defects. Autograft bone is said to be osteoinductive; that is it will grow bone wherever it is placed in the body due to the cellular content and the presence of growth factors. Despite the generally favorable results from autograft transplants, there remain serious concerns about donor site morbidity, graft collapse and length of hospital stay in comparison to using other materials. Allograft bone in various forms has also been used extensively as bone grafts with mixed results. Allograft, while yielding outcomes generally similar to autograft, is expensive to produce, is generally slower to incorporate, and is variable in performance due to different processing methods and carries the potential risk of infection and disease transmission, though that risk is quite small.

Due to the issues with autograft and allograft bone, a number of other materials, including xenograft and synthetic biomaterials have been used in various bone grafting procedures. Hydroxyapatite bone substitutes have been used somewhat successfully in certain long bone fractures. These materials are said to be osteoconductive. That is, they allow bone to grow along the surface of the material and actually act as a scaffold for new bone growth. This osteoconductive ability depends on the composition, physical structure, porosity and method of manufacture of these materials.

Hydroxyapatite materials have been used mainly in dental procedures and in some long bone grafting procedures. In cervical fusion procedures there have been few reports of the use of synthetic hydroxyapatite. In a clinical study by Zdeblick, coralline-derived HA (ProOsteon, Interpore Cross, Irvine, Calif.) was evaluated in non-instrumented cervical fusion with less than half the grafts incorporating. In that study 14% of grafts extruded and 29% collapsed. Tri calcium phosphates are another form a ceramic material that is used, usually in a porous form for non-load bearing bone grafts. While the success has been good in small defects, the particulate material is somewhat difficult to work with and cannot always be maintained in the surgical site.

Calcium sulfate materials are a form of highly resorbable ceramic bone graft substitute. These have been used with some success as well, but are again limited in their use due to the particulate nature of the material and the difficulty of keeping it in the surgical site. In addition, there have been reports that the material resorbs too quickly, leaving bone voids and poor clinical outcomes. In addition to the synthetic bioceramic materials, there has been some attempt to use xenograft bone for repair and regeneration. However, there is always a risk of antigenicity from this bone, derived mainly from the atelo groups on the collagen fibers within the bone structure. There is also a fear of transmission of CJD (Crutzfeld Jacobs Disease) from the bovine source, although the risk is actually quite small. However, these elements have severely limited its use.

Calcium, sodium phosphosilicate materials, commonly referred to as bioactive glasses are another class of bioceramic material that has been successfully used in bone graft procedures. Calcium sodium phosphosilicates are unique in that they are not only osteoconductive but are also osteostimulative. When exposed to an aqueous environment, such as found in bony defects, the material releases specific ions (Ca, P, Si, Na) in certain concentrations over time. Due to this release of ions, the surface changes and becomes an excellent structure to support cell adhesion, proliferation and differentiation.

Numerous in-vitro and in-vivo studies have shown that these compounds stimulate the rapid proliferation and differentiation of osteoblasts compared with other bone graft materials. In-vitro studies have demonstrated that exposure of osteoblasts to bioactive glass actually upregulates a family of genes that are involved in cellular proliferation as well as differentiation into an osteoblasts phenotype. Additional studies have demonstrated that the ionic extracts released from the bioactive glass particles can actually upregulate primary osteoblasts compared with control samples, accelerating the rate of cell differentiation. Earlier cell culture studies with primary osteoblasts had shown that after 21 days, three-dimensional bone nodules greater than 3 mm in length had formed when cultured on bioactive glass disks. Recent studies have also demonstrated that certain concentrations of the extracts released from bioactive glasses have a pro-angiogenic response. This property would be especially important in the early stages of wound healing and creating an environment favorable for new bone formation. In light of the results with the ionic extracts described and the surface reactive nature of the bioactive glass when exposed to an aqueous environment, those results are consistent with our knowledge of these materials and help to explain the robust bone regenerative properties of this material.

Recently, a clinical study was published comparing bioactive glass (NovaBone, NovaBone Products, LLC) with autograft in adolescent idiopathic scoliosis cases. The average follow-up was 40 months. The results showed a higher complication rate with autograft compared with the bioactive glass (not statistically significant) and a greater loss of correction with autograft compared with the bioactive glass ($p=0.025$) which was statistically significant. In addition, blood loss was significantly less in the bioactive glass group (1280 mL in the autograft group versus 853 mL in the bioactive glass group). The authors concluded that bioactive glass was effective as a bone graft in these procedures and performed equivalently with autograft. However, in the particulate form, bioactive glass particles are limited by the same constraints as the other bioceramic materials.

In an attempt to improve on the use of particulate materials, there have been a number of composite and putty-like materials that have been developed for bone regeneration. Because calcium phosphate materials are very similar to bone mineral these have been incorporated with many other bioresorbable and non-resorbable polymers. One of the most often cited and used materials in this regard is collagen, because the combination of the calcium phosphate and collagen is close in composition to natural bone. In one example a solid composite is formed by taking collagen from about 5% up to 75% and precipitating a calcium salt and a phosphate containing salt to form a homogeneous composite (U.S. Pat. No. 5,320,844). While this produces a workable material, it is limited by the size and shape because the precipitation of the soluble calcium and phosphate materials will preferentially occur on the surface and the composition of the composite will vary throughout the structure. This would naturally lead to variable properties of the material.

Another variation of this precipitation process is disclosed in U.S. Pat. No. 6,395,036, where a matrix of a bioresorbable polymer (collagen) is exposed to different solutions of calcium ions and phosphate ions such that there is more hydroxyapatite in the body of the composite than on the surface. This is achieved through careful control of pH and concentration of the ionic solutions as well as the order and rate at which they are exposed to the collagen matrix.

The U.S. Pat. No. 6,187,047 describes a process where dilute solutions of collagen, type I, are mixed with fine particles of calcium phosphate, where the particles are 5 microns or less. This process forms a porous 3-dimensional matrix that maintains its structural integrity for at least 3 days and maintains porosity for up to 14 days. While this method allows for the immobilization of the particles initially, once the material starts to degrade, the release of small particles can be problematic is it is know that small particles can cause an osteolytic process that results in inflammation and bone resorption.

U.S. Pat. No. 6,417,166 discloses a thin flexible mineralized collagen membrane for such uses as guided barrier membranes and periodontal defect repair as well as bone grafts and wound repair. The process utilizes up to 70% collagen with 30% to 70% calcium phosphate minerals. The process relies on the addition of calcium solutions and phosphate solutions to a collagen slurry and casting the slurry into a mold and drying said mixture. This is said to form a mineralized collagen composite. This process is severely limited, however, to thin small membranes as the process is ineffective and very expensive for making larger shapes and forms.

Other examples of collagen-calcium phosphate composites can be found in U.S. Pat. No. 6,764,517 and U.S. Pat. No. 6,902,584. In these patents, a 3-dimensional mineralized collagen composite is produced by creating collagen slurry, freezing and lyophilizing the mixture and then subjecting it to calcium and phosphate solutions to form a porous mineralized matrix. These patents further describe adding a soluble collagen in an additional step and lyophilizing that mixture to form the porous composite. The inventions further describe the ability to use various cross-linking agents to enhance physical stability and increased implant resonance time and shape retention. While this technology can produce an improvement over the previous technologies, the manufacturing process consists of many different steps which become costly and very time consuming.

Further refinements of these general methods for producing collagen—calcium phosphate composite materials can be found in U.S. Pat. No. 7,156,880 and U.S. Pat. No. 7,166,133. These inventions describe the manufacture of implants that consist of an osteoconductive matrix that comprises a blend of both insoluble and soluble collagen where at least a portion of the implant is porous. In addition these structures may contain osteoinductive molecules as well as biodegradable synthetic polymers. The patents also describe the incorporation of ceramic materials such as calcium phosphate, calcium sulfate or hydroxyapatite in the form of discrete particles, rather than forming the compounds through precipitation of salts.

More recent technologies, such as those found in U.S. Pat. No. 7,531,004 and U.S. Pat. No. 7,534,451 describe a bone restorative composite material that consists of a resorbable polymer that can be collagen, a range of meso, micro and macro porosity to allow for the inclusion of fluid and to assist in bone ingrowth, as well as the inclusion of calcium phosphate particles. The patents further describe a specific oxidation-reduction reaction of very specific calcium and phosphorous containing salts to precipitate calcium phosphate within the collagen structure. These devices typically require very precise control of the chemistry in order to obtain the desired results of the precipitation of the calcium phosphate materials and appear to be limited to calcium based osteoconductive materials.

While the above referenced composite materials and methods of their delivery are an improvement over the use of particulate materials there is still a need for a cost-effective material that can be widely used in bone regenerative surgery, and that will enhance the bone healing. While calcium phosphate materials are osteoconductive the osteostimulative effects of calcium-sodium phosphosilicate materials such as described above would enhance the robustness of bone healing. Such materials could also carry additional bio-molecules, growth factors or other therapeutic agents. There is also need for improved delivery methods, kits and systems. Therefore, it is an object of this invention to provide a cost effective, easily manufactured bone restorative material that enhances the bone regeneration of damaged osseous tissue, will remain in the surgical site, and gradually resorb over time to leave only natural bone tissue in the regenerated site as well as methods, kits and system for delivery of the bone restorative material.

SUMMARY

Figure 1:
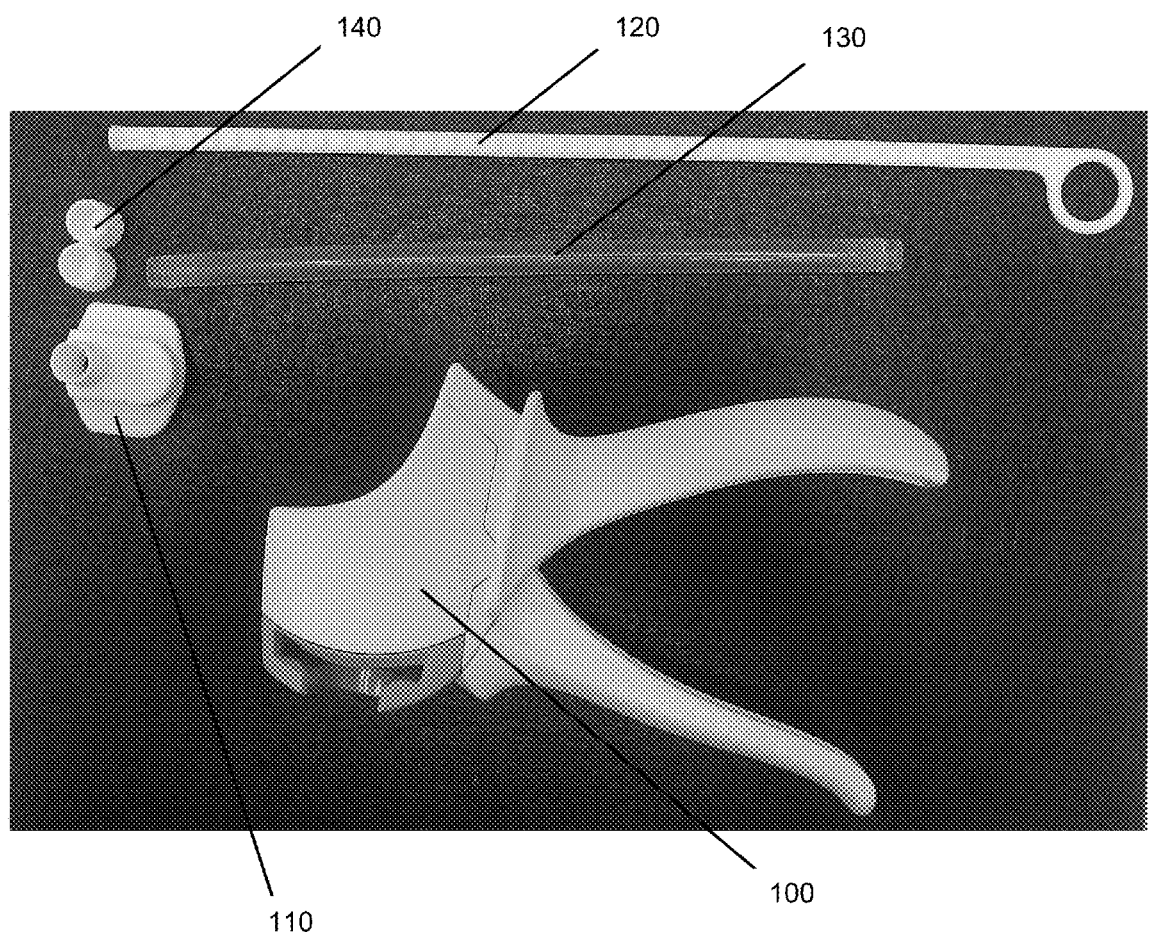
FIG. 1 depicts an exemplary delivery system kit for delivering a composition for regenerating bone.

The use of an extracellular matrix protein collagen in combination with bioactive glass ceramic, which contains silica or boron, is disclosed. The protein component of the compositions provides amino acids which upon resorption of the collagen provide the building blocks (amino acids) for cells to produce a new collagen matrix which is mineralized during the bone regeneration process. The bioactive glass ceramic component undergoes an ion exchange with the surrounding body fluid to form hydroxyapatite analogous to bone mineral. In addition, the ceramic of the present invention releases calcium and silicate or calcium and borate ions which facilitate the differentiation and proliferation of osteoblasts (defined as osteostimulation), which increases the rate of regeneration of hard tissue. More specifically, dissolution of these bioactive glass ceramics release, calcium and silicate or calcium and borate ions, which stimulate the genes responsible for the differentiation and proliferation of osteoblast cells within the bony defect upon implantation. This genetic response is activated through introducing and maintaining critical concentrations of calcium and silica or borate ions. This activation of the genetic cascade responsible for osteoblast proliferation and differentiation subsequently promotes the increased rate regeneration of hard tissue. These composites also provide a three dimensional scaffold for (bone forming cells) osteoblasts to reside to facilitate the regeneration of hard tissues.

One embodiment relates to a kit for a minimally invasive delivery of a composition for regenerating bone at or near the site of a bony defect. The kit includes at least one tube comprising the composition for regenerating bone comprising about 2-60% collagen and about 40-98% bioactive glass, wherein the at least one tube is capped when not in use, a dispensing gun, an adapter and a plunger. The kit, optionally, includes one or more dispensing tips. The components of the kit are snap fit into a tray and a retainer is placed to maintain position of the components in the tray. The tray holds up to four tubes comprising the composition for regenerating bone. The kit may further include a syringe. The kit may also include a "Y" connector, tube connector, or an aspiration needle, or a combination thereof. The bioactive glass of the composition for regenerating bone has a porosity of up to 90%. The bioactive glass has pores ranging from about 1 to about 5100 microns. The bioactive glass has average pore size of <50 microns; alternatively, the bioactive glass has average pore size of 100 microns plus or minus 50 microns; alternatively, the bioactive glass has average pore size of 200 microns plus or minus 50 microns; alternatively, the bioactive glass has average pore size of 300 microns plus or minus 50 microns; alternatively, the bioactive glass has average pore size of 400 microns plus or minus 50 microns; alternatively, the bioactive glass has average pore size of 500 microns plus or minus 50 microns; alternatively, the bioactive glass has average pore size of 600 microns plus or minus 50 microns; alternatively, the bioactive glass has average pore size of 700 microns plus or minus 50 microns. The composition for regenerating bone of the kit includes about 3-60% collagen and about 40-97% bioactive glass; alternatively, the composition for regenerating bone includes about 3-50% collagen and about 50-90% bioactive glass. The composition for regenerating bone may further include an extracellular matrix molecule selected from the group consisting of integrins, fibronectin, vitronectin, osteopontin, bone sialoprotein thrombospondin, and fibrinogen, or a homo or copolymer of glycerol, glycols, glycolides, acrylates, lactic acids or other organic acids, and caprolactone. The composition for regenerating bone may be un-crosslinked or crosslinked. The composition for regenerating bone may be freeze-dried. The composition for regenerating bone may be in a lyophilized form. The bioactive glass of the composition for regenerating bone of the kit may be pre-reacted with a buffer. The bioactive glass comprises 55-65% 1000-2000 um bioactive glass, 10-20% 90-710 um bioactive glass, and 10-20% 32-125 um bioactive glass; alternatively, the bioactive glass comprises 60% 1000-2000 um bioactive glass, 12.5% 90-710 um bioactive glass, and 12.5% 32-125 um bioactive glass. The 1000-2000 um bioactive glass may be porous. The composition for regenerating bone may be in a form of a collagen bioactive glass composite, wherein the collagen bioactive glass composite is lyophilized, or wherein the collagen and bioactive glass composite is lyophilized and crosslinked. The composition for regenerating bone, where the composition is in a form of a mixture of collagen in a granular, particulate, sphere or bead form, or a combination thereof, and bioactive glass in a granular, particulate, sphere or bead form, or a combination thereof. The composition for regenerating bone wherein the composition is in a granular, particulate, sphere or bead form, or a combination thereof, and comprises collagen and bioactive glass. The composition for regenerating bone of the kit may further comprise at least one therapeutic agent, a signaling protein, or glycosaminoglycan. The bioactive glass of the composition for regenerating bone may be in a granular form, particulate form, matt form, fiber form, hemostatic sponge form, foam form, paste or putty form, or sphere or bead form, or a combination thereof. The composition for regenerating bone may be pre-treated with water, saline, blood, bone marrow, a combination thereof, or other biocompatible substance to form a paste. The bioactive glass may include silicate based glasses or borate based glasses.

A further embodiment relates to a method for repairing or regenerating a bony defect comprising dispensing the composition for regenerating bone comprising about 2-60% collagen and about 40-98% bioactive glass at or near the site of the bony defect using the components of the kit described herein. In the method, the composition for regenerating bone is moldable upon mixing with saline, blood, bone marrow, or other biocompatible fluid. In the method, the composition for regenerating bone may be pre-treated with water, saline, blood, bone marrow, a combination thereof, or other biocompatible substance to form a paste.

DETAILED DESCRIPTION

The present application relates to compositions, systems, kits and methods suitable for bone regeneration and/or treatment of bone defect(s). In some aspects, the compositions, systems, kits and methods relate to composite structures with enhanced bone regeneration capabilities, and which remain in the surgical site, adsorb body fluids, blood, bone marrow aspirate and hold other biomolecules. The composite structure is a composition for regenerating bone that includes bioactive materials, such bioactive glass and collagen.

Bioactive materials suitable for the present invention are any surface active materials able to chemically bond to body tissue. Examples of bioactive materials suitable for the compositions, systems, kits and methods include bioactive glasses, glass ceramics and ceramics. Bioactive glasses are typically amorphous whereas bioactive glass ceramics typically contain crystalline particles embedded in an amorphous glass phase. Bioactive ceramics typically have a crystalline structure. Thus, the bioactive materials may be amorphous, crystalline or combinations thereof (i.e., amorphous particles having some crystalline domains, crystalline particles having some amorphous domains or mixtures of crystalline and amorphous particles).

The bioactive material may be prepared by any suitable technique known to those skilled in the art. For example, the particles may be native calcium phosphate or sodium phosphosilicate particles (amorphous bioactive glass particles), or combinations thereof. The calcium phosphate materials may be naturally occurring or synthetic. The calcium phosphate may be amorphous or crystalline or combinations thereof. Illustrative calcium phosphates have the general chemical formula $Ca_5(PO_4)_3X$, where X is OH (hydroxyapatite), F (fluorapatite), or Cl (chlorapatite). Such materials are also known as "apatites." The term "hydroxyapatite" or "HA" as used herein, generally refers to a form of apatite with the formula $Ca_5(PO_4)_3(OH)$. More typically, HA is represented as $Ca_{10}(PO_4)_6(OH)_2$ to denote that the crystal unit cell comprises two molecules. Hydroxylapatite is the hydroxylated member of the complex apatite group. The hardness of hydroxyapatite may be altered by replacing the OH ion with other anions (e.g., fluoride, chloride or carbonate). Additionally, HA has a relatively high affinity for peptides, making it an ideal carrier for the delivery and sustained release of polypeptides over long periods of time in situ.

In some embodiments, sodium phosphosilicate particles and calcium phosphate particles may be present in the compositions in an amount of about 1% to about 99%, based on the weight of sodium phosphosilicate particles and calcium phosphate particles. In further embodiments, calcium phosphate may be present in the composition in about 1%, about 2%, about 3%, about 4%, about 5%, about 6%, about 7%, about 8%, about 9%, or about 10%. In certain embodiments, calcium phosphate may be present in the composition in about 5 to about 10%, about 10 to about 15%, about 15 to about 20%, about 20 to about 25%, about 25 to about 30%, about 30 to about 35%, about 35 to about 40%, about 40 to about 45%, about 45 to about 50%, about 50 to about 55%, about 55 to about 60%, about 60 to about 65%, about 65 to about 70%, about 70 to about 75%, about 75 to about 80%, about 80 to about 85%, about 85 to about 90%, about 90 to about 95%, or about 95 to about 99%. Some embodiments may contain substantially one of sodium phosphosilicate particles and calcium phosphate particles and only traces of the other. The term "about" as it relates to the amount of calcium phosphate present in the composition means±0.5%. Thus, about 5% means 5±0.5%.

In certain embodiments, the particles may have particular size and/or geometry. For example, the particles may be spherical (e.g., microspheres) or may possess any other geometry such as flat surfaces (e.g., microdisks). In some embodiments, the particle size may be about 50 microns to about 5 mm in diameter. In some embodiments, the average particle size is about 500 to about 1500 microns, about 1000 to about 2000 microns or from about 1200 micron to about 2500 microns. In certain embodiments, the particles may have average diameter of about 50, about 100, about 200, about 500, about 750, about 1000, about 1200, about 1400, about 1600, about 1800, about 2000, about 2200, about 2500, about 2750, about 3000, about 3500, about 4000, about 4500, or about 5000 microns. In some embodiments, the bioactive glass particle has a diameter of between about 1 micrometer and about 2,000 micrometers. As used in this paragraph, the term "about" means±100 microns or ±10% of the average particle size, whichever is smaller. Thus, about 50 microns means 50±5 microns whereas about 3500 microns means 3500±100 microns.

In certain embodiments, the bioactive material may be a bioactive glass or glass ceramic. The bioactive material may be calcium phosphate or calcium sodium phosphosilicate particles.

Bioactive glass may be melt-derived or sol-gel derived. Depending on their composition, bioactive glasses may bind to soft tissues, hard tissues, or both soft and hard tissues. The composition of the bioactive glass may be adjusted to modulate the degree of bioactivity. Furthermore, borate may be added to bioactive glass to control the rate of degradation. Additional elements, such as barium, copper, fluorine, silver, zinc, and strontium may be added to bioactive glass to facilitate healthy bone growth or provide other desirable properties. The bioactive glass may be in the form of a particle, a glass sheet, a fiber, a mesh, or any combination of these forms.

Bioactive glass is capable of bonding to bone, which begins with the exposure of bioactive glass to aqueous solutions. Sodium ions in the glass can exchange with hydronium ions in body fluids, which increases the pH. Calcium and phosphorous ions can migrate from the glass to form a calcium and phosphate-rich surface layer. Borate ions can also migrate from the glass to from a surface layer rich in boron. Strontium ions also can migrate from the glass to form a strontium-rich surface layer. Underlying this surface layer is another layer which becomes increasingly silica rich due to the loss of sodium, calcium, strontium, boron, and/or phosphate ions (see, e.g., U.S. Pat. No. 4,851,046). Hydrolysis may then disrupt the Si—O—Si bridges in the silica layer to form silanol groups, which can disrupt the glass network. The glass network is then thought to form a gel in which calcium phosphate from the surface layer accumulates. Mineralization may then occur as calcium phosphate becomes crystalline hydroxyapatite, which effectively mimics the mineral layer of bones.

Bioactive glass particles, fibers, meshes or sheets may be prepared by a sol-gel method. Methods of preparing such bioactive active glasses are described in Pereira, M. et al., "Bioactive glass and hybrid scaffolds prepared by sol-gel method for bone tissue engineering" Advances in Applied Ceramics, 2005, 104(1): 35-42 and in Chen, Q. et al., "A new sol-gel process for producing $Na_2O$-containing bioactive glass ceramics" Acta Biomaterialia, 2010, 6(10):4143-4153.

The composition can be allowed to solidify. In some embodiments, particles of bioactive glass are sintered to form a porous glass.

Repeated cooling and reheating may be performed on the solidified or sintered bioactive glass, with or without spinning, to draw the bioactive glass produced into fibers. A glass drawing apparatus may be coupled to the spinner and the source of molten bioactive glass, such as molten bioactive glass present in a crucible, for the formation of bioactive glass fibers. The individual fibers can then be joined to one another, such as by use of an adhesive, to form a mesh. Alternatively, the bioactive glass in molten form may be placed in a cast or mold to form a sheet or another desired shape.

A bioactive glass material may have silica, sodium, calcium, strontium, phosphorous, and boron present, as well as combinations thereof. In some embodiments, sodium, boron, strontium, and calcium may each be present in the compositions in an amount of about 1% to about 99%, based on the weight of the bioactive glass ceramic. In further embodiments, sodium, boron, strontium and calcium may each be present in the composition in about 1%, about 2%, about 3%, about 4%, about 5%, about 6%, about 7%, about 8%, about 9%, or about 10%. In certain embodiments, silica, sodium, boron, and calcium may each be present in the composition in about 5 to about 10%, about 10 to about 15%, about 15 to about 20%, about 20 to about 25%, about 25 to about 30%, about 30 to about 35%, about 35 to about 40%, about 40 to about 45%, about 45 to about 50%, about 50 to about 55%, about 55 to about 60%, about 60 to about 65%, about 65 to about 70%, about 70 to about 75%, about 75 to about 80%, about 80 to about 85%, about 85 to about 90%, about 90 to about 95%, or about 95 to about 99%. Some embodiments may contain substantially one or two of sodium, calcium, strontium, and boron with only traces of the other(s). The term "about" as it relates to the amount of calcium phosphate present in the composition means +/−0.5%. Thus, about 5% means 5+/−0.5%. Divalent cations or ions that may be present in any of the bioactive glasses of this and other aspects of the invention include one or more of iron-II, iron-III, alumina, chromate, cobalt, titania, zirconia, copper, magnesium, and zinc. Additionally, silver and gold may be added to the composition for additional therapeutic benefits.

The bioactive glass materials may further comprise one or more of a silicate, borosilicate, borate, strontium, or calcium, including SrO, CaO, $P_2O_5$, $SiO_2$, and $B_2O_3$. An exemplary bioactive glass is 45S5, which includes 46.1 mol % $SiO_2$, 26.9 mol % CaO, 24.4 mol % $Na_2O$ and 2.5 mol % $P_2O_5$. An exemplary borate bioactive glass is 45S5B1, in which the $SiO_2$ of 45S5 bioactive glass is replaced by $B_2O_3$. Other exemplary bioactive glasses include 58S, which includes 60 mol % $SiO_2$, 36 mol % CaO and 4 mol % $P_2O_5$, and S70C30, which includes 70 mol % $SiO_2$ and 30 mol % CaO. In any of these or other bioactive glass materials, SrO may be substituted for CaO.

In certain embodiments, bioactive glass may include glasses having about 40 to about 60 wt-% $SiO_2$, about 10 to about 34 wt-% $Na_2O$, up to about 20 wt-% $K_2O$, up to about 5 wt-% MgO, about 10 to about 35 wt-% CaO, up to about 20 wt-% $B_2O_3$, about 0.5 to about 12 wt-% $P_2O_5$. The bioactive glass may additionally contain up to 10-wt % $CaF_2$. In certain embodiments, the bioactive glass has the following composition 53 wt-% $SiO_2$, 6 wt-% $Na_2O$, 12 wt-% $K_2O$, 5 wt-% MgO, 20 wt-% CaO, and 4 wt-% $P_2O_5$. Other compositions are also suitable.

In some embodiments, the bioactive glass is 45S5 bioactive glass. The 45S5 bioactive glass may vary in size from 1 micrometer to 5 millimeters. The bioactive glass may be about 1-5 micrometers, about 5-15 micrometers, about 15-50 micrometers, about 50-200 micrometers, about 200-1,000 micrometers, about 1-2 millimeters, about 2-3 millimeters, about 3-4 millimeters, or about 4-5 millimeters.

The following composition, having a weight % of each element in oxide form in the range indicated, will provide one of several bioactive glass compositions that may be used to form a bioactive glass:

| | |
|---|---|
| $SiO_2$ | 0-86 |
| CaO | 4-35 |
| $Na_2O$ | 0-35 |
| $P_2O_5$ | 2-15 |
| $CaF_2$ | 0-25 |
| $B_2O_3$ | 0-75 |
| $K_2O$ | 0-8 |

-continued

| | |
|---|---|
| MgO | 0-5 |
| CaF | 0-35 |

In some embodiments, the particles are sintered to form porous particulate made from the bioactive glass particles. In one embodiment, fine particles of the bioactive glass are mixed with a sacrificial polymer and a binder to create a pre-shaped construct (e.g., a block or disk). The construct is then heated under specific conditions that allow a welding of the particles together without completely melting them. This process uses a temperature high enough to allow for the polymer material to burn off leaving a porous structure. The compression strength as well as the porosity of the construct may be controlled by varying the type and the amount of the sacrificial polymer and the sintering time and temperature used. Porosities as high as 90% may be achieved under suitable conditions. The pores in the bioactive glass material range from about 10 microns to about 5100 microns with an average pore size of 100±50 microns, 200±50 microns, 300±50 microns, 400±50 microns, 500±50 microns, 600±50 microns or 700±50 microns.

The bioactive glass ceramic can be in the form of a three-dimensional compressible body of loose glass-based fibers, in which the fibers comprise one or more glass-formers selected from the group consisting of $P_2O_5$, $SiO_2$, and $B_2O_3$. Some of the fibers have a diameter between about 100 nm and about 10,000 nm, and a length:width aspect ratio of at least about 10. The pH of the bioactive glass can be adjusted as-needed.

In some embodiments, the body comprises fibers having a diameter between about 100 nm and about 10,000 nm. The especially small diameter of these fibers renders them highly flexible so they form into the compressible body without breaking. In some embodiments the body includes fibers meeting these dimensional requirements in addition to other glass morphologies, such as fibers of other dimensions, spheres, microspheres, particles, ribbons, flakes or the like. The fibers may have a variety of cross section shapes, such as flat, circular, oval, or non-circular.

In certain embodiments, fine particles of the bioactive glass are mixed with a sacrificial polymer and a binder to create a pre-shaped construct (e.g., a cylinder, block or disk). The construct is then heated under specific conditions that allow welding of the particles together without completely melting them. This process uses a temperature high enough to allow for the polymer material to burn off leaving a porous structure. The compression strength as well as the porosity of the construct may be controlled by varying the type and the amount of the sacrificial polymer and the sintering time and temperature used.

Porosities as high as 90% may be achieved under suitable conditions. The pores in the bioactive glass material range from about 10 microns to about 5100 microns with an average pore size of 100±50 microns, 200±50 microns, 300±50 microns, 400±50 microns, 500±50 microns, 600±50 microns or 700±50 microns. In certain embodiments, the bioactive glass has average pore size of <50 microns.

The bioactive glass material may be ground with mortar and pestle prior to converting it to a paste. Any other method suitable for grounding the bioactive glass material may be used.

In certain embodiments, the bioactive glass material is be mixed with other constituents to produce templates or granules that may be formed into a paste that can be shaped and/or incorporated into kits before further treatments are made. For example, a suitable bioresorbable polymer may be used to prepare a composite in a form of a paste of a bioactive material (for example, glass or ceramic material) and bioresorbable polymer. In one embodiment, a paste of a non-crystalline, porous bioactive glass or ceramic material is prepared that permit in vitro formation of bone tissue when exposed to a tissue culture medium and inoculated with cells.

A bioresorbable polymer may be any biological polymer that facilitates cell adhesion, including but not limited to integrins, collagens, fibronectin, vitronectin, osteopontin, bone sialoprotein thrombospondin, fibrinogen, or combinations thereof.

Thus, in some embodiments, the bioactive glass may be mixed with integrins or other extracellular matrix molecules, such as various forms of collagens, fibronectin, glycosaminoglycans, vitronectin, osteopontin, bone sialoprotein thrombospondin, and fibrinogen. Other suitable bioresorbable polymers may include homo and copolymers of glycolides, acrylates, lactic acids, and caprolactone. Additional bioresorbable polymers suitable for the present invention are those described in U.S. Pat. Nos. 6,322,797, 6,238,687, 6,166,173, 6,153,212, and 5,912,225, each of which is hereby incorporated by reference. In some embodiments, the composition for regenerating bone may further comprise a polysaccharide (such as dextran, dextran sulfate, diethylaminoethyl dextran, or dextran phosphate or mixtures thereof).

In certain embodiments, the composition for regenerating bone comprises about 2-60% collagen and about 40-98% bioactive glass. Alternatively, a bone regenerative composition comprises about 3-60% collagen and about 40-97% bioactive glass; and preferably, about 3-50% collagen and about 50-97% bioactive glass.

In certain embodiments, the composition for regenerating bone may be in a form of a collagen-bioactive glass composite. The collagen-bioactive glass composite may be lyophilized and/or crosslinked. In certain other embodiments, the composition for regenerating bone may be in a form of a mixture of (a) collagen in a granular form, particulate form, matt form, fiber form, hemostatic sponge form, foam form, paste or putty form, or sphere or bead form, or a combination thereof; and (b) bioactive glass in a granular form, particulate form, matt form, fiber form, hemostatic sponge form, foam form, paste or putty form, or sphere or bead form, or a combination thereof. Preferably, the composition for regenerating bone includes about 2-60% collagen and about 40-98% bioactive glass. Alternatively, a bone regenerative composition comprises about 3-60% collagen and about 40-97% bioactive glass; and preferably, about 3-50% collagen and about 50-97% bioactive glass.

In certain further embodiments, the composition for regenerating bone may be in a granular form, particulate form, matt form, fiber form, hemostatic sponge form, foam form, paste or putty form, or sphere or bead form, or a combination thereof, and include collagen and bioactive glass. Preferably, the composition for regenerating bone includes about 2-60% collagen and about 40-98% bioactive glass. Alternatively, a bone regenerative composition comprises about 3-60% collagen and about 40-97% bioactive glass; and preferably, about 3-50% collagen and about 50-97% bioactive glass.

In some embodiments, collagen may be Type I collagen that may be used as the bioresorbable polymer of the composition for regenerating bone. Type I collagen is the most plentiful in the body and has been widely used for medical applications. It can be derived from bovine, ovine or other sources. In some embodiments, collagen is extracted from the native source, for example, bovine hides using a neutral or dilute acidic buffer. In this extraction process, a slurry of collagen in an aqueous buffer, either acidic around pH 3 or by a slightly different process a neutral pH around 7, is produced. In another form of production, the acid treated collagen is further broken down enzymatically to remove the telo peptides at the end of the collagen chains. This treatment renders the collagen more soluble and may lessen any possible antigenicity caused by the telo groups on the ends of the collagen fibrils. The concentration of the collagen varies anywhere from 3 mg/mL of solution to upwards of 50 mg/mL. The samples were evaluated for wickability and retention of fluids after wetting. To achieve this, the samples (in triplicate) were cut into 1 inch×1 inch sizes. Liquids such as water, saline or sheep blood were used in 1:1 volumetric ratio dependent on the sample size. Liquids were added in increments (drops) to the strip and the wicking property was evaluated dependent on the absorption time of the liquids and the volume of fluids required to completely saturate the samples.

Wicking Evaluation Parameters:
Sample absorption ratio—with a desired volume ratio of 1:1 or more;
Absorption time—the shorter the better with 1-2 seconds deemed acceptable;
After wetting, the samples that did not require any manipulation for complete saturation were deemed desirable;
Samples that wet thoroughly through all surfaces were deemed desirable;

After wetting, the samples were evaluated for shrinkage, homogeneity, fluid retention and structural integrity. After wetting the samples were measured to verify the size and calculate the shrinkage if any. Shrinkage of 5-10-% upon wetting was considered acceptable.

After wetting, the samples were visually inspected for homogeneity making sure the particles were uniformly distributed in the composite samples. A 100 g calibration standard weight was placed on the wetted samples to evaluate the fluid retention property.

Fluid retention evaluation parameters:
After wetting, a 100 g calibrated weight standard was placed on the samples;
The samples were typically able support the weight of the standard without collapsing;
With a 100 gm load, desirable samples typically retained 90%-100% of the fluid. Samples were evaluated visually and fluid retention capability of the samples were evaluated by counting the drops of fluid expressed out after weight placement;

The samples were manipulated to evaluate the structural integrity. Upon manipulation desirable samples exhibit some level of shape/memory retention quality. Desirable samples retain a level of moisture, maintaining consistency without disintegrating.

In the initial experiments, it was found that the reactivity (ionic release) of the bioactive glass particles caused a reaction with the collagen used that prevented an adequate working time to allow for the shaping and subsequent processing of the implants. This resulted in a material that would not absorb liquid and resulted in poor handling characteristics. Ability to absorb liquid is important in the performance of the implanted material.

In certain further embodiments, the composition for regenerating bone may comprise any one or more of adhesives, grafted bone tissue, in vitro-generated bone tissue, collagen, calcium phosphate, stabilizers, antibiotics, antibacterial agents, antimicrobials, drugs, pigments, X-ray contrast media, fillers, and other materials that facilitate grafting of the composition for regenerating bone to bone.

The silica and/or calcium ions released by the bioactive glass may improve the expression of osteostimulative genes. The silica and/or calcium ions may also increase the amount of and efficacy of proteins associated with such osteostimulative genes. In several embodiments, the bone repair material is osteostimulative and can bring about critical ion concentrations for the repair and regeneration of hard tissue without the necessity of any therapeutic materials or agents.

In certain embodiments, bioactive glass can be mixed with water, buffer, saline, blood, bone marrow or other biocompatible fluid to produce a paste.

In certain embodiments, it is surprisingly been found that when the paste of a composition for regenerating bone including pre-treated bioactive glass or ceramic particles and a bioresorbable polymer is freeze-dried, it retains the osteostimulative effect of the glass while retaining its physical integrity and remaining wettable. Thus, in one embodiment, the composition for regenerating bone including bioactive glass or ceramic particles and collagen is treated with water, certain buffer solutions, saline, blood, bone marrow aspirate or other biocompatible fluid prior to the preparation of the paste. The composition for regenerating bone may also be pre-treated with bone-morphogenetic proteins, platelet-rich plasma, and osteogenic proteins. The pre-treatment prepares the surface of the bioactive particles for cell adhesion and controls pH prior to the exposure of the particles with cells. In certain embodiments, the bioactivity and bone formation using the glass particles of the present invention may be enhanced by treating the glass particles with water, certain buffer solutions, saline, blood, bone marrow aspirate or other biocompatible fluid prior to mixing the bioactive glass particles with a bioresorbable polymer (i.e., collagen).

In certain embodiments, the pre-treatment solution has a starting pH of from about 6 to about 8 but may reach an end pH of about 9.5.

Examples of buffers that might be suitable for the pre-treatment of the present invention include mixed sodium phosphate salts (such as Sorensen's Phosphate buffer, Millonig's Phosphate buffer, Karlsson and Shultz Phosphate buffer, Maunsbach Phosphate buffer, and Phosphate Buffered Saline (PBS); buffer pH of about 6.4-8.0), TAPS (3-{[tris(hydroxymethyl)methyl]amino}propanesulfonic acid; buffer pH of about 7.7-9.1), Bicine (N,N-bis(2-hydroxyethyl)glycine; buffer pH of 7.6-9.0), Tricine (N-tris(hydroxymethyl)methylglycine; buffer pH about 7.4-8.8), Tris(tris(hydroxymethyl)methylamine; buffer pH of about 7.5-9.0), HEPES (4-2-hydroxyethyl-1-piperazineethanesulfonic acid; buffer pH of about 6.8-8.2), TES (2-{[tris(hydroxymethyl)methyl]amino}ethanesulfonic acid; buffer pH of about 6.8-8.2), MOPS (3-(N-morpholino)propanesulfonic acid; buffer pH of about 6.5-7.9), PIPES (piperazine-N,N'-bis(2-ethanesulfonic acid); buffer pH of about 6.1-7.5), Cacodylate (dimethylarsinic acid; buffer pH of about 5.0-7.5), SSC (saline sodium citrate; buffer pH of about 6.5-7.5), or MES (2-(N-morpholino)ethanesulfonic acid; buffer pH of about 5.5-6.7). Any other buffer having appropriate pH buffering range of about 6 to about 8 might be suitable.

In certain embodiments, the end pH does not exceed 9.5, 9.4, 9.3, 9.2, 9.1, 9.0, 8.8, 8.9, 8.7, 8.6, 8.5, 8.3, 8.2, 8.1, or 8.0.

Depending on the pre-treatment method used, the composition for regenerating bone or the bioactive glass or ceramic particles may be pretreated for different periods such that the particles become suitable for preparing constructs suitable for bone regeneration. Pre-treating the bioactive glass or ceramic particles much longer than necessary to activate them may deactivate the particles. Similarly, if the bioactive glass or ceramic particles are not pre-treated long enough, they may remain too active and attempts to convert them into a paste may encounter premature gellation of the paste. In some embodiments, the bioactive glass or ceramic particles may be pretreated with water, certain buffer solutions, saline, blood, bone marrow aspirate or other biocompatible fluid for as short as 30 minutes. Other embodiments of the bioactive glass may require pretreatment as long as 24 hours. In some embodiments, the bioactive glass may be pretreated about 1 to about 2 hours, about 3 to about 4 hours, about 5 to about 6 hours, about 7 to about 8 hours, about 9 to about 10 hours, about 11 to about 12 hours, about 13 to about 14 hours, about 15 to about 16 hours, about 17 to about 18 hours, about 19 to about 20 hours, about 21 to about 22 hours, or about 23 to about 24 hours. Some bioactive glasses may require pretreatments longer than 24 hours. As used here in the context of pre-treatment time, the term "about" means±30 minutes. A person skilled in the art can easily design simple experimental procedures to determine the optimum pretreatment time for bioactive glass or ceramic particles using water, buffer solutions, saline, blood, bone marrow aspirate or other biocompatible fluid.

A paste of the pre-treated bioactive glass or ceramic particles and a bioresorbable polymer may be prepared using methods known to those skilled in the art. The paste may then be shaped into a desirable form, left un-crosslinked or, optionally crosslinked, and freeze dried before contacting the freeze-dried paste with a culture medium or implanted into an animal.

In certain embodiments as described in connection with the kit below, the paste may be used to fill the tubes of the kit or delivery system. Once inside the tubes, the paste may be dried. Drying process includes and may not be limited to air drying, vacuum drying, or freeze drying (lyophilized).

Thus, one embodiment of the present invention relates to methods of forming a composition for regenerating bone comprising providing bioactive material (e.g., porous bioactive glass particles), immersing the bioactive material in a pre-treatment solution (e.g., water, certain buffer solutions, saline, blood, bone marrow aspirate or other biocompatible fluid), isolating the pre-treated particles, forming a paste of the pre-treated particles and a bioresorbable polymer (e.g., collagen), shaping the paste to a construct with the desired shape, and freeze-drying the construct. The freeze-dried construct so obtained may be immersed in a tissue culture medium to produce a construct having enhanced bone cell activity when cells are inoculated on its surface. In certain embodiments, the construct is inoculated with cells and bone tissue is permitted to form thereon.

The properties of the construct, i.e. porosity, pore size and compressive strength, can be adjusted to a desired level by adjusting the amount and type of the bioresorbable polymer used to prepare the paste, the choice of the particle size, the pre-treatment solution used to pre-treat the particles, and length of time the particles are exposed to the pre-treatment solution.

In certain embodiments, the lyophilized construct may be subjected to crosslinking or a fixation treatment to preserve the structural integrity of the construct. Any reagent suitable for fixation/crosslinking of biological constructs may be suitable. Such fixation/crosslinking may include exposing the freeze-dried construct to gluteraldehyde and may occur without any mechanical, hydrostatic, or other external stress placed on the construct. Fixing the construct without application of external stress would allow for some shrinkage of the construct to occur without affecting the orientation of the bioresorable polymer or the biomechanical properties of the construct.

In certain embodiments, the construct is inoculated with cells and bone tissue is permitted to form thereon. In further embodiments, the construct is inoculated with cells from the patient by implanting the construct in a patient. In certain embodiments, the construct is inoculated with osteoblasts or precursor cells to osteoblasts. The osteoblasts or the precursor to the osteoblasts may have been extracted from the patient that is to receive the construct as an implant. In certain embodiments, the osteoblasts or its precursor may be extracted from a donor. In further embodiments, the porous bioactive glass constructs may be implanted in sites where there is an immediate need for bone.

Further embodiments relate to kits and delivery systems for minimally invasive delivery of a composition for regenerating bone at or near the site of a bony defect or hard tissue defect. Specifically, the kit includes a composition for regenerating bone comprising about 2-60% collagen and about 40-98% bioactive glass.

In certain embodiments, the composition for regenerating bone as part of the kit and delivery system may be in a form of a collagen-bioactive glass composite. The collagen-bioactive glass composite may be lyophilized and/or crosslinked.

In certain other embodiments, the composition for regenerating bone as part of the kit and delivery system may be in a form of a mixture of (a) collagen in a granular form, particulate form, matt form, fiber form, hemostatic sponge form, foam form, paste or putty form, or sphere or bead form, or a combination thereof; and (b) bioactive glass in a granular form, particulate form, matt form, fiber form, hemostatic sponge form, foam form, paste or putty form, or sphere or bead form, or a combination thereof. Preferably, the composition for regenerating bone includes about 2-60% collagen and about 40-98% bioactive glass. Alternatively, a bone regenerative composition comprises about 3-60% collagen and about 40-97% bioactive glass; and preferably, about 3-50% collagen and about 50-97% bioactive glass.

In certain further embodiments, the composition for regenerating bone as part of the kit and delivery system may be in a granular form, particulate form, matt form, fiber form, hemostatic sponge form, foam form, paste or putty form, or sphere or bead form, or a combination thereof, and include collagen and bioactive glass. Preferably, the composition for regenerating bone includes about 2-60% collagen and about 40-98% bioactive glass. Alternatively, a bone regenerative composition comprises about 3-60% collagen and about 40-97% bioactive glass; and preferably, about 3-50% collagen and about 50-97% bioactive glass.

A further embodiment relates to a kit for minimally invasive delivery of a composition for regenerating bone at or near the site of a bony defect or hard tissue defect that includes at least one tube including a composition for regenerating bone comprising about 2-60% collagen and about 40-98% bioactive glass, wherein the at least one tube is capped or sealed (e.g., sealed with foil) when not in use. The kit also includes a dispensing gun, an adapter, a plunger, and optionally, one or more dispensing tips. Other optional components of the kit include a syringe, aspiration needle, or other suitable delivery device and accompanying accessories.

Figures 2A, 2B:
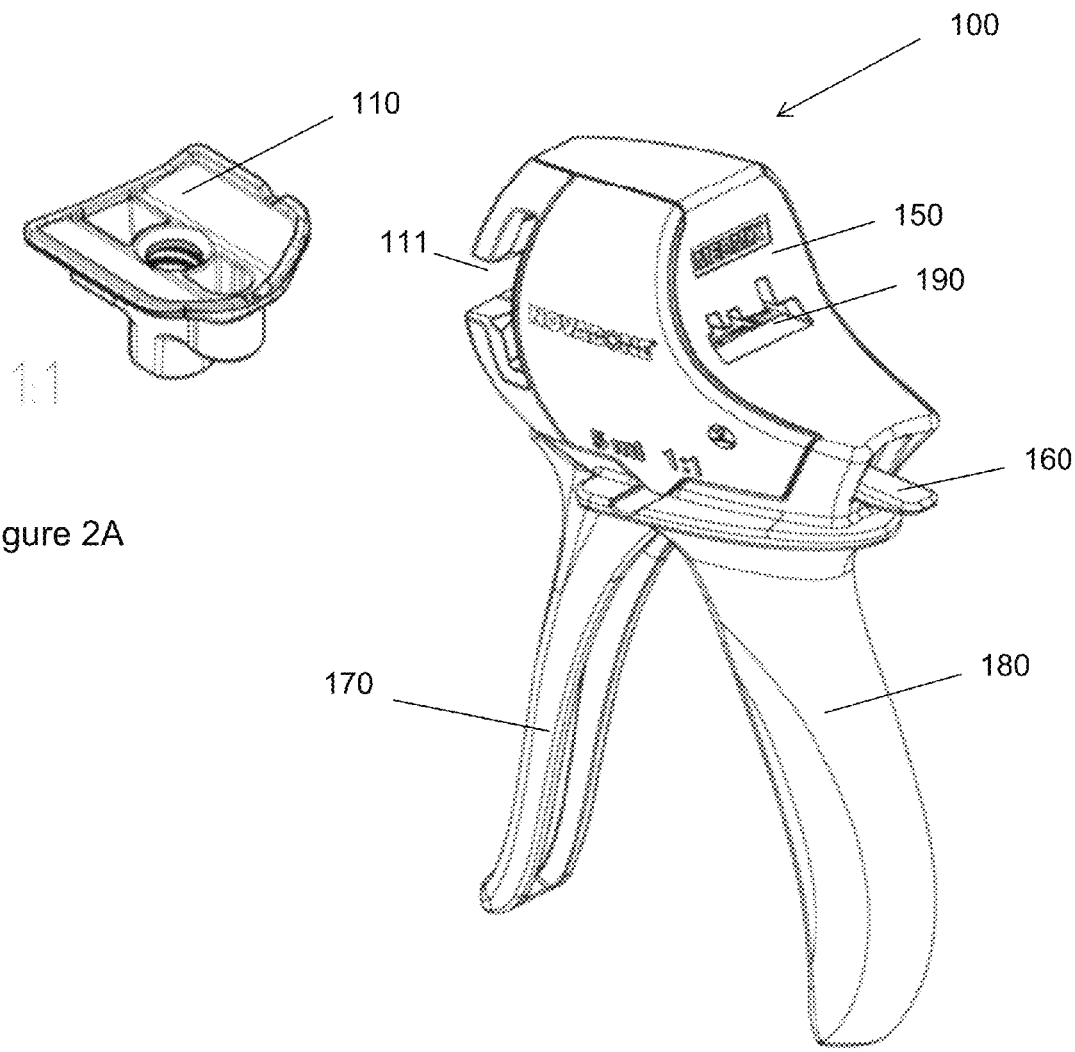
FIG. 2A-B depicts schematic drawings of an adapter (2A) and a delivery gun (2B) for the composition for regenerating bone.
Figure 4:
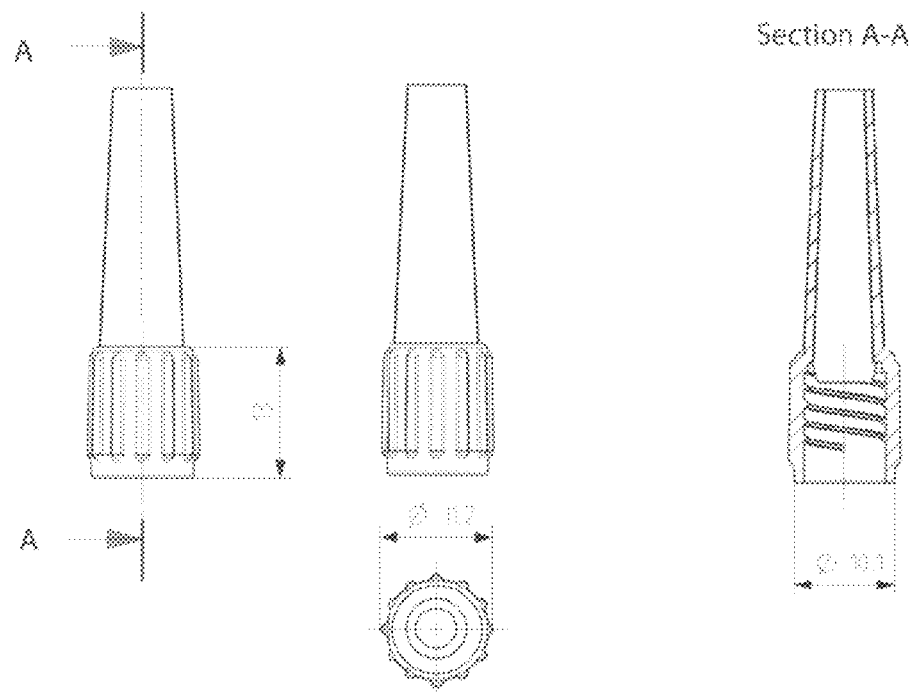
FIG. 4A depicts exemplary tips for a delivery system.
FIG. 4B depicts exemplary tips for a delivery system.
Figure 4B:
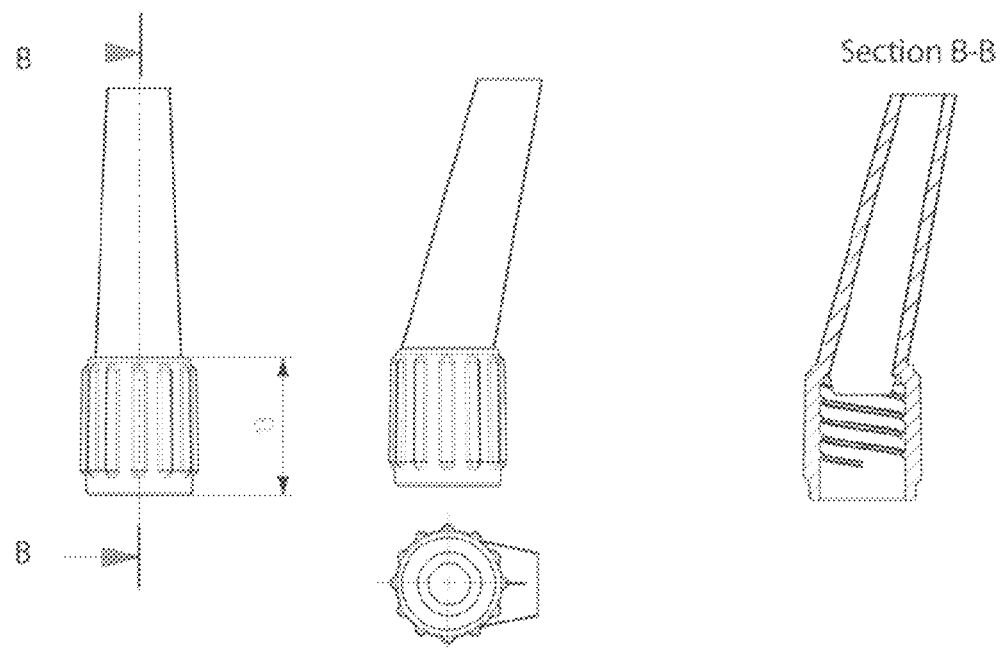
Figure 5A:
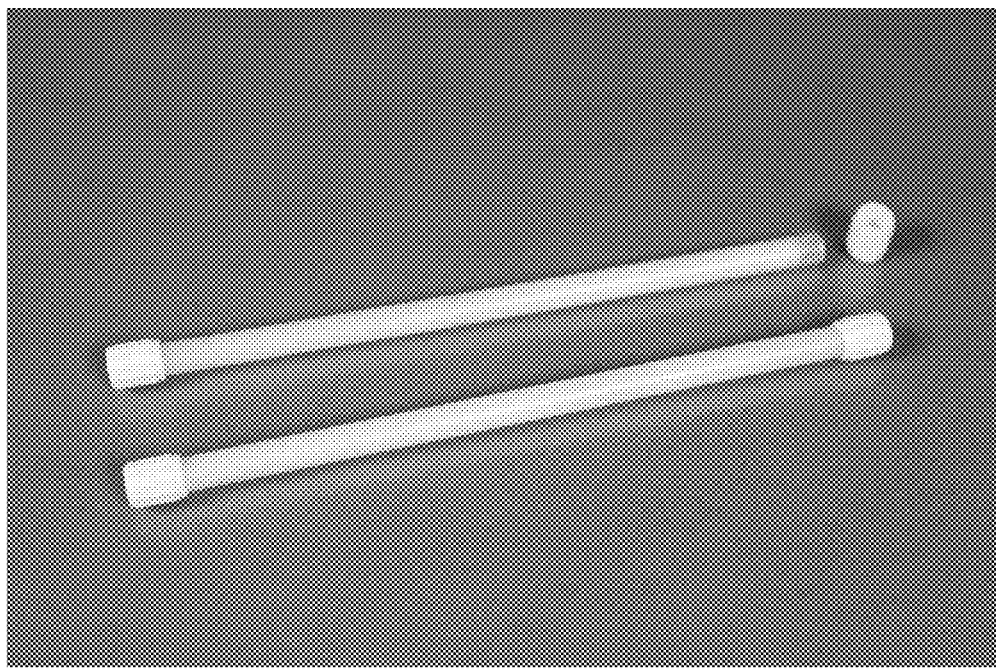
FIG. 5A is a photograph of the tubes filled with a composition for regenerating bone for use with a delivery system.

Specifically, referring to FIGS. 1 and 2A-B, the exemplary dispensing gun 100, adapter 110, plunger 120 (see also FIG. 3), tube(s) 130 (see also FIGS. 5A and 5B), caps 140, and assorted dispensing tips (optional; FIG. 4A and FIG. 4B) that may be included with the kits are shown. The composition for regenerating bone may be deposited into the tube(s) 130 as part of the kit (FIG. 5A). An exemplary kit for delivery of other materials, such as Bioactive Synthetic Bone Graft Putty is currently being sold by NOVABONE® (NOVABONE® Bioactive Synthetic Bone Graft Putty MIS Cartridge Delivery System, NovaBone Products, LLC, Alachua, Fla.).

Referring to FIGS. 2A-B, the dispensing gun 100 may include a cover 150, a latch 160, a lever 170 and a handle 180 (FIG. 2B). The adapter 110 (shown also in FIG. 2A) may be inserted into the dispensing gun at an opening 111. A plunger (not shown) may be inserted through the front of the gun and pushed through the opening in the back 190 of the gun.

Figure 3:
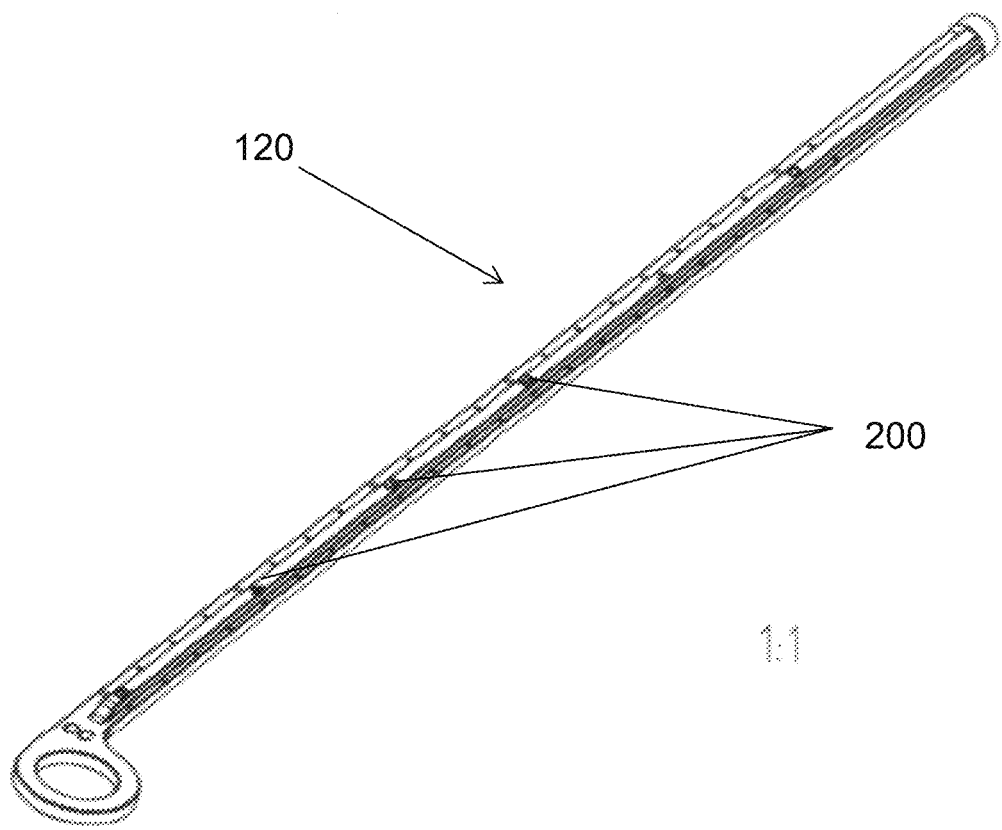
FIG. 3 depicts a schematic drawing of a plunger of the delivery system.

FIG. 3 depicts an exemplary plunger 120 including gradient markings 200 facing up.

FIGS. 4A-B depict exemplary tips for use with the dispensing gun. The tips may be straight (FIG. 4A) or at an angle (FIG. 4B) and their inclusion in the kit and subsequent use are optional.

Figure 5B:
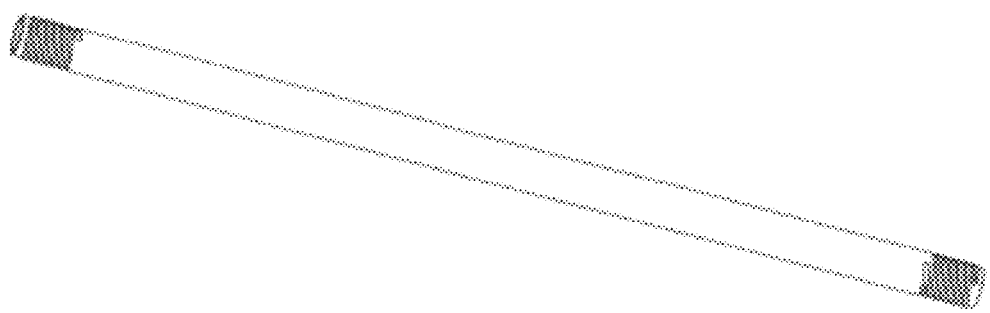
FIG. 5B depicts a schematic drawing of a tube for use with a delivery system.

FIG. 5A is a picture of tubes filled with the composition for regenerating bone; FIG. 5B is a graphical illustration of an exemplary tube for use with the kit and specifically with the delivery gun described above. The tubes have a substantially constant inner diameter along their entire length such that the outlets have substantially the same inner diameters as the rest of the tubes.

Figure 9:
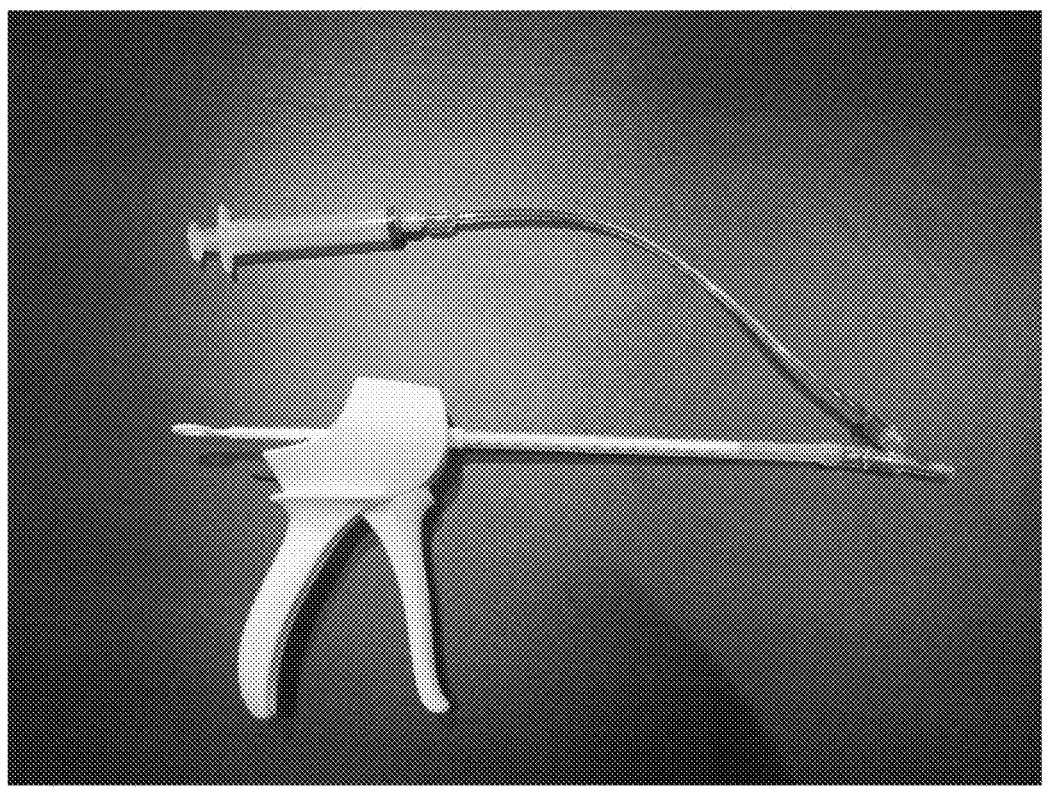
FIG. 9 is a photograph of an exemplary delivery system for a composition for regenerating bone.

Optionally, a "Y" connector, luer syringe and a tube connector may be included to facilitate the simultaneous delivery of biologics or other grafting materials and to maintain position during shipping (as shown in FIG. 9).

The components of a kit may be packaged and sold as a kit. The components of a kit may snap fit into a (inner) tray of a packaging and a retainer may be placed over the components of the kit to maintain position of the components during shipping. The inner tray may hold up to four tubes that can be prefilled with the irrigation resistant bone repair composition and capped on each end. The inner tray may also contain cavities for the placement of assorted tips, a "Y" connector, tube connector, a syringe and aspiration needle.

The inner tray may be sealed with a lid and placed into an outer tray also sealed with a lid. The sealed trays are radiation sterilized for use in medical applications. The sealed trays may then be placed in a box.

Immediately prior to use, the kit may be placed in an operating room and the outer tray is opened. The inner tray is removed by a sterile technician and placed into the sterile field.

Figure 6A:
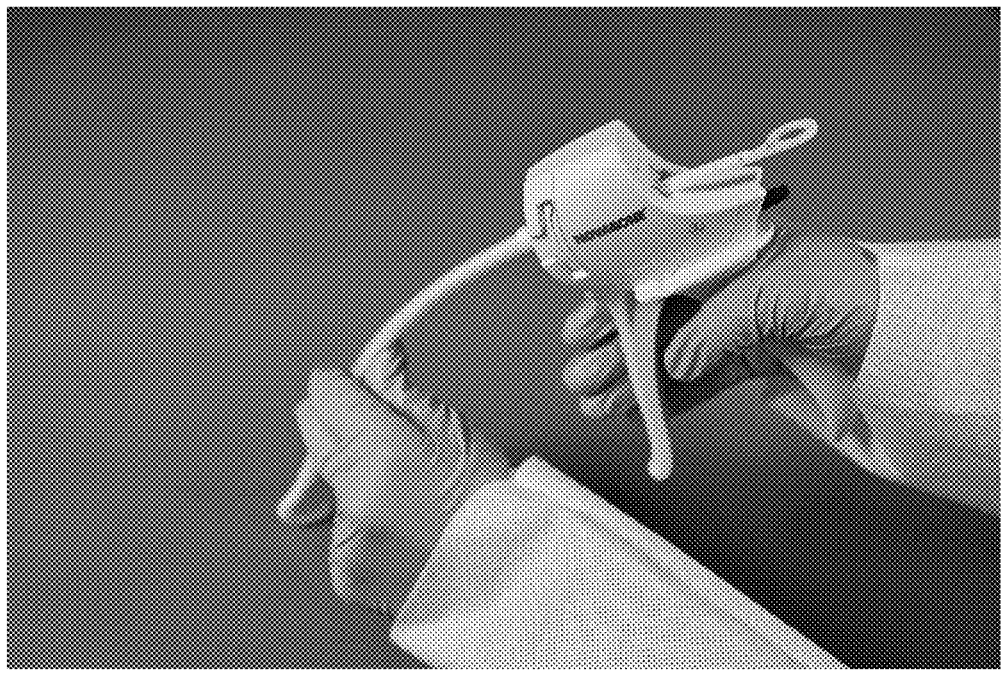
FIG. 6A is a photograph of an exemplary delivery system for a composition for regenerating bone.
Figure 6B:
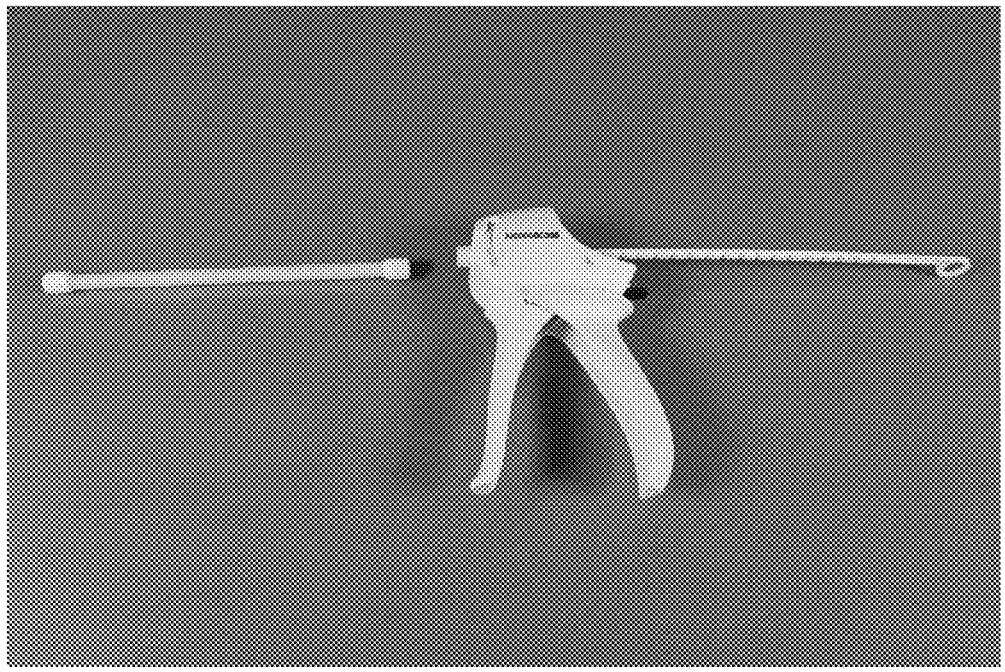
FIG. 6B is a photograph of an exemplary delivery system for a composition for regenerating bone.
Figure 7:
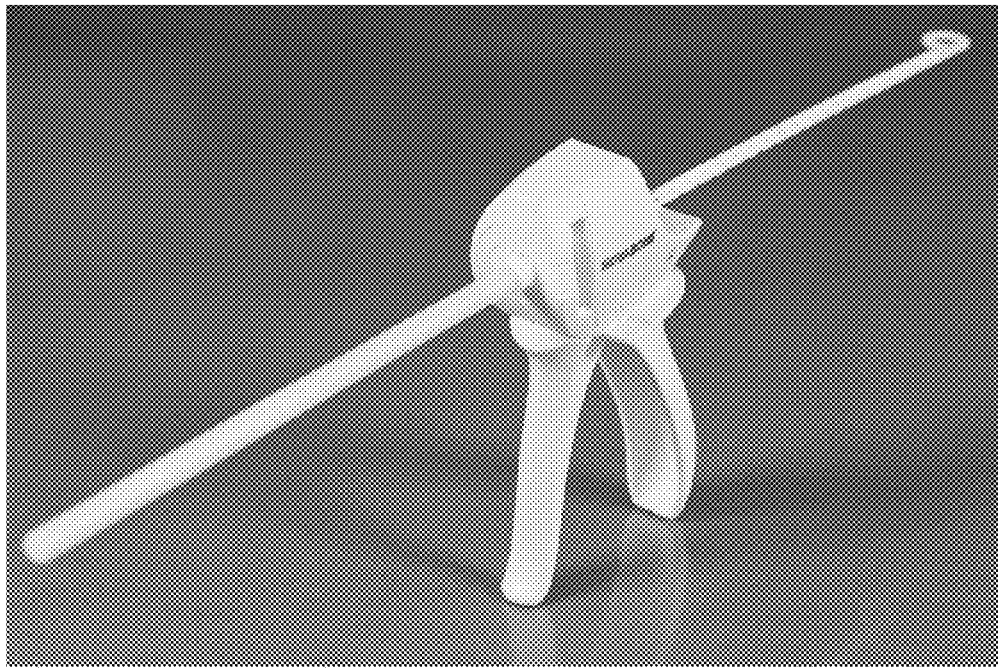
FIG. 7 is a photograph of an exemplary delivery system for a composition for regenerating bone.
Figure 8:
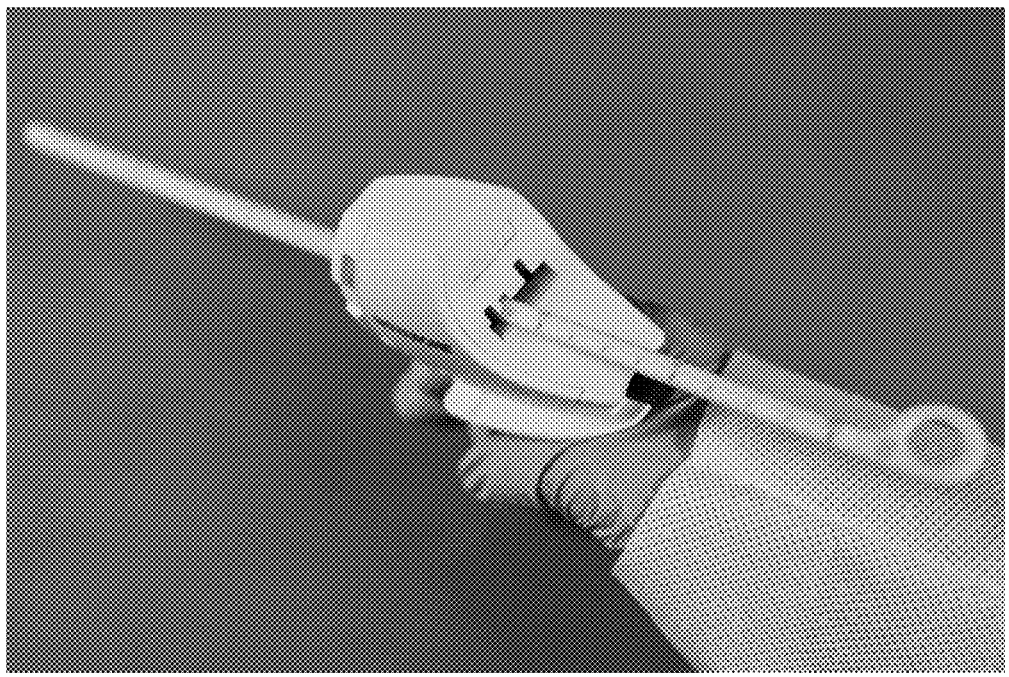
FIG. 8 is a photograph of an exemplary delivery system for a composition for regenerating bone.

In the sterile field the inner tray is opened and the dispensing gun is assembled by inserting the finger grip of the plunger 120 (with the gradient markings 200 facing up and teeth facing down) through the opening in the front of the gun 100 and pushing the plunger through the back of the gun until the piston end of the plunger is seated completely within the gun (see FIGS. 6A, 7 and 8). The adapter 110 is then inserted into the front of the gun 100. Next a prefilled tube is removed from the inner tray. One cap is removed from the prefilled tube. The tube is threaded into the adapter and the other cap is removed from the tube (FIG. 6B). Optionally a tip can be placed on the end of the tube to direct the flow of the graft material.

The tip of the instrument may be placed into the surgical site. Upon pressing the trigger of the gun, the plunger is ratcheted forward to express the composition for regenerating bone into the surgical site. The dispensing gun consists of, a handle, in which a block is moved forward through pressing the trigger which engages the teeth of the plunger moving the piston forward displacing the material from the tube. The trigger is manually disengaged by pushing the lever at the back of the dispensing gun upward allowing the plunger to be pulled back to a starting position. The first tube can be removed from the adapter and additional tubes can be threaded in place as needed.

Another embodiment involves altering the adapter for the attachment of two tubes and the plunger modified from a single piston to one have two pistons moving simultaneously with each compression of the trigger. Subsequently, the plungers dispense the composition for regenerating bone from the two tubes through a static mixer to facilitate the addition of a biological or drug material into the non-setting bone grafting material during injection into the surgical site. Any of the above-described aspects and embodiments of the invention may be in injectable form. Injection may occur by means of a syringe, for example. The compositions are particularly useful when injected in a gel or liquid form into a bone gap or bone defect. The injected gel or liquid would then solidify at body temperature when placed on or near the bone gap or the bone defect.

EXPERIMENT 1

Three type I collagens were used in the following experiments: (a) acid swollen gel ("ASG") pH 3, (b) digested, pepsin treated collagen (higher solubility) ("DM3"), or (c) base treated gel, pH 7, all at 10 mg/mL concentration. To the collagen slurry, suspension, solution, or gel, is was added 90% bioactive glass, porous particles, 1 mm-2 mm size range. The particles were mixed with the collagen slurry using a low speed mixer and the resultant mixture was poured into a mold. It was noted that during mixing the viscosity of the solution began increasing prior to pouring the mixture, indicating that ions released from the particles, specifically Na, Ca or Si were interacting with the active side chains of the collagen causing something of a cross-linking of the chains. After getting the slurry into the molds, the mixture was lyophilized (i.e., frozen and then subjected to a vacuum in order to sublime the frozen water). This process resulted in a dry collagen-particulate matrix. Upon placing drops of water on the surface of the material it was noted that there was no adsorption of the liquid, indicating that the reaction of the particles with the collagen in the mixing vessel had rendered the material relatively inactive.

EXPERIMENT 2

In these experiments, the acid swollen gel ASG was mixed with the pepsin treated collagen DM3 at 1:2, 1:1 and 2:1 ratios. The total collagen concentration used was 10 mg/mL along with a 97% by weight concentration of particles. The particles were mixed with the collagen slurry and it was noticed that the slurry began to gel prior to pouring into the molds, just as in the previous experiment. After the lyophilization process was complete, the resulting materials were wetted and again it was noted that liquid was not absorbed into the material. It was also noted that particles of the bioactive glass were falling out of the composite material upon handling.

EXPERIMENT 3

In this experiment, the particle size of the bioactive glass was reduced to 800 microns to 1.7 mm and a combination of ASG/DM3 collagen at a 2:1 ratio was used. The loading of the particulates was lowered from 97% to 95%. The outcome was similar to that in Experiment 2 in that the mixture was noted to react in the mixer and the slurry began to gel, limiting the working time of the mixtures. In addition, while this ratio of the ASG to DM3 collagen allowed for some adsorption of liquid when tested after the lyophilization process, the handling characteristic resulted in a material that did not hold together after wetting.

From the above experiments it appears that using particles of bioactive glass in the native state results in material that is too reactive to allow for the proper open pore structure of the collagen-particulate composite, and changes the surface so that it is not possible to adsorb the fluids that are so important to the proper functioning of the device. Therefore, one embodiment of the present invention is to pre-react the particles in such a manner that the surface ionic reactivity would be reduced enough so that the particles did not interfere with the proper setting of the collagen structure while maintaining enough reactivity so that the composite material exhibited the unique osteostimulative properties imparted by the bioactive glass particles. Therefore, one pre-reaction matrix was set up in order to reduce the surface ionic activity enough to allow proper formation of the composite materials. The process of pre-reacting the particulate depends on the particle size, volume of particles used and the reagent used. Because the reactivity is sensitive to the surface area of particles exposed to the solution and to the volume of the solution, it will be appreciated that the examples below are only for the specific volumes and mass of particles used. The process consists of reacting a specific weight of particulate, in this case 25 g of particles with a surface area of 1 $m^2/g$ in 200 ml of a tris hydroxyl-aminomethane (TRIS) buffer that is titrated to a pH of 7.2 using hydrochloric acid. Particles were reacted for 1, 2, 6, 12 and 18 hrs and the starting and ending pH measured. The rise in pH is related to the amount of ions released from the particles.

| Date | Sample | Start pH | End pH | Particle Size |
|------|--------|----------|--------|---------------|
| 8/25 | P1 hr | 7.32 | 8.08 | 1-2 mm |
| 8/25 | P18 hr | 7.31 | 8.73 | 1-2 mm |
| 8/25 | BG1p | 7.34 | 8.75 | 1-2 mm |
| 8/25 | BG18p | 7.32 | 9.35 | 1-2 mm |
| 9/21 | P6p | 7.21 | 8.77 | 1-2 mm |
| 9/21 | P6p | 7.21 | 8.77 | 1-2 mm |
| 9/22 | P12p | 7.25 | 9.15 | 1-2 mm |
| 9/22 | P18p | 7.21 | 9.24 | 1-2 mm |
| 9/23 | P6p #1 | 7.21 | 8.89 | .8-1.4 mm |
| 9/23 | P6p #2 | 7.21 | 8.98 | .8-1.4 mm |
| 10/14 | P18p #1 | 7.33 | 9.42 | .8-1.4 mm |
| 10/14 | P18p #2 | 7.33 | 9.49 | .8-1.4 mm |
| 10/14 | P18p #3 | 7.33 | 9.36 | .8-1.4 mm |
| 10/14 | P18p #4 | 7.33 | 9.42 | .8-1.4 mm |
| 10/14 | P18p #5 | 7.33 | 9.22 | .8-1.4 mm |
| 10/14 | P18p #6 | 7.33 | 9.24 | .8-1.4 mm |

P = porous particles
BG = solid bioactive glass control

The table above shows the various porous particles and control bioactive glass that was pre-reacted. These various iterations were used in further experiments with the collagen materials to form composites.

EXPERIMENT 4

The same collagen blend as in experiment 3 (2:1 ASG/DM3 at 10 mg/mL) was used along with porous particles that were pre-reacted at either 1 hr or 18 hours. The processing was the same for all samples. The 1 Hr pre-reacted samples behaved in the same manner as the unreacted particles; that is they did not absorb fluid readily, the material was fairly dense and not as porous as collagen alone, and when finally wet it did not retain the particles. The samples produced with the 18 Hr pre-reacted particles fared much better. There was little pH rise after mixing, the slurry was able to be mixed and poured into molds before the slurry gelled, and the particles were retained in the composite. In addition, when liquid was placed on the surface of these samples the material adsorbed the liquid quite rapidly. In addition, the handling properties of the composite that used the pre-reacted particles were superior to the other samples.

There are a few other examples of passivating the surface of bioactive glass particles or subjecting them to solutions that contain proteins in order to make a surface that contains a reacted hydroxyapatite layer with proteins intermingles. In U.S. Pat. No. 5,977,204 bioactive glass particles are used as a filler in a resorbable polymer matrix. The surface passivated bioactive glass is reacted for 3 days in order to form a complete hydroxyapatite layer. It was found that this surface reacted layer produced a composite that had enhanced mechanical properties. The invention describes the passivation of the bioactive glass as being made incapable of reacting with water. This technology would prevent the bioactive glass particles in the current invention from further enhancing the bone regeneration through the further release of ions to the surrounding tissue and would therefore not be applicable to the composite devices of the current invention.

In U.S. Pat. No. 6,224,913 (and U.S. Pat. No. 6,413,538 and U.S. Pat. No. 6,549,466) the bioactive glass particles are subjected to repeated immersions in a number of different solutions in order to incorporate proteins within the hydroxyapatite layer that forms as a result of reactions. The presence of proteins within the bioactive particle surface would likely have adverse reactions with the side chains of the organic collagen molecule and the result would likely be constructs that do not absorb fluid and could possibly cause inflammatory responses.

We discovered that there is a limited range of reactivity of bioactive glass particles that forms a very thin HCA layer that isn't completely covering the surface of the particles and still allows the further reaction of the particles to release the ions that enhance bone regeneration and still provide the osteo-stimulative response of the composite.

EXPERIMENT 5

ASG/DM3 collagen, at 20 mg/mL was mixed with 90% by weight of 0.85 mm-1.4 mm bioactive glass particles. Two sets of particles were used; one pre-reacted for 6 hours and one reacted for 18 hours. In both cases, the slurry pH did not rise significantly after mixing in the particles; the material was mixed for 2 minutes and cast into molds. It was then placed in the lyophilizer and the samples were freeze-dried. Upon removal the materials were homogeneous, porous and of a uniform consistency. The samples all absorbed moisture rapidly, and when handled after the absorption of the liquid, they all maintained their structural integrity.

In addition to the above mentioned examples, it is possible, after the lyophilization process, to cross-link the composite, either with gluteraldehyde, or other chemical or enzymatic agents. The cross-linking will enhance the mechanical and structural integrity of the composites and will also improve the fluid adsorption.

EXPERIMENT 6

Two variations using 1:1 & 2:1 ASG/DM3 collagen ratios at 20 mg/ml were mixed with 90% by weight of 0.85 mm-1.4 mm bioactive glass particles. 18 hr pre-reacted particles were used and the slurry was poured into molds and cast. After the first lyophilization, the constructs were chemically crosslinked using glutaraldehyde in various concentrations. Three different concentrations of glutaraldehyde were used: 0.00125 (low), 0.0125 (med) & 0.125 (high) to evaluate the structural integrity and manipulation properties of the samples. The samples were tested for wicking ability as well as mechanical handling. The lowest and the medium concentration crosslinked samples remained homogenous and maintained uniform consistency.

EXPERIMENT 7

In this experiment, two levels in concentration of the chemical crosslinking agent glutaraldehyde between the lowest and the medium levels were evaluated for the next set of samples. $6.25 \times 10^{-3}$ & $9.4 \times 10^{-3}$ levels of glutaraldehyde were used keeping the particle size of 18 hr pre-reacted bioactive glass particles at 0.85 mm-1.4 mm and the collagen ratio (ASG/DM3) at 2:1. The samples were evaluated again for their handling properties and wickability with equal volume of liquids.

EXPERIMENT 8

The next experiments involved incorporation of smaller particle sizes into the pre-reacted bioactive glass mixture. The new samples that were generated used 0.5 mm-1.4 mm particles. Collagen ratio was constant as previous experiment ASG/DM3 @ 2:1 and the slurry was poured into molds and lyophilized. Upon removal from the first lyophilization cycle, the samples were treated with two levels of crosslinking: $6.25 \times 10^{-3}$ & $9.4 \times 10^{-3}$. The samples again were evaluated for homogeneity and structural integrity after absorption of an equal volume of liquid

EXPERIMENT 9

The next set of experiments evaluated the effect of lyophilization on varying sizes of the samples. Two sizes of samples: 25 mm×50 mm×4 mm & 25 mm×50 mm×8 mm were generated using 90% by weight of 0.5 mm-1.4 mm pre-reacted bioactive glass morsels mixed with 2:1 ASG/DM3 collagen @ 20 mg/ml and chemically crosslinked at $6.25 \times 10(-3)$ using glutaraldehyde. The samples obtained were evaluated again for homogeneity, shrinkage and structural integrity after wetting.

EXPERIMENT 10

Preparation of Packable Graft

A "Packable graft" as defined herein is a loose collagen and 45S5 bioactive glass mixture that becomes moldable when hydrated.

The control sample "1" was prepared by hydrating 100% collagen with DI WATER (reverse osmosis deionized water prepared using the Sartorius system) until the material became moldable and then by forming a 2.5 cc sphere. The sphere was then soaked in DI WATER for 24 hours.

The test samples "2", "3", and "4" were prepared by combining 1-2 mm, 90-710 μm 45S5 bioglass, and 32-125 μm 45S5 bioglass with collagen. The dry materials were then hydrated with varying $CaCl_2$ solutions and then soaked in DI WATER for 24 hours.

Test samples "5" and "7" were prepared similarly to Samples 2-4 except HCl was used to adjust the pH of the different percent $CaCl_2$ solutions to 6.5.

Test sample "6" was prepared by replacing 5 wt % of the 32-125 μm 45S5 bioactive glass with ionomer glass, in particular ionomer glass powder TF-325. The packable graft was then hydrated and soaked in DI WATER.

The samples were evaluated on the Shimadzu Mechanical Strength Tester using compressive plates and a 1 kN Load cell. Tests were conducted under ambient conditions and all samples were tested in accordance with SOP PR-06.06 Mechanical Testing of CBG Product. The indenter displacement was set to 25 mm with a rate of 15 mm/min. The load was released when a max strength of 900 N or a max stroke of 30 mm was obtained.

The following table illustrates the composition and the compressive strength of the Packable graft samples that were evaluated.

| | Dry Composition (wt %) | | | | Hydrating | Soaking | Compressive Strength |
|---|---|---|---|---|---|---|---|
| ID | Collagen | Bioglass | Misc. | Size (cc) | Soln. | Soln. | (kPa) |
| 1 | 100 | 0 | 0 | 2.5 | RODI | RODI | 7.22424 |
| 2 | 15 | 85 | 0 | 2.5 | 0.1% CaCl$_2$ | RODI | 37.5007 |
| 3 | 15 | 85 | 0 | 2.5 | 0.25% CaCl$_2$ | RODI | 51.3565 |
| 4 | 15 | 85 | 0 | 2.5 | 1% CaCl$_2$ | RODI | 63.7604 |
| 5 | 15 | 85 | 0 | 2.5 | 0.5% Ca(Cl)$_2$ pH 6.5 | RODI | 105.645 |
| 6 | 15 | 80 | 5% Ionomer Glass | 2.5 | RODI | RODI | 128.284 |
| 7 | 15 | 85 | 0 | 2.5 | 1% Ca(Cl)$_2$ pH 6.5 | RODI | 148.51 |

The data in Table 1 indicates that after soaking, packable graft containing bioactive glass is stronger than a packable graft containing only collagen (control sample 1). The data for test samples 3-5 and 7 indicates that the increasing concentration of Ca$^{2+}$ ions in the hydration solution increases the compressive strength. Test sample 6 was prepared with the same hydrating and soaking solutions as the control (sample 1) and exhibited higher compressive strength because of the presence of the bioactive and ionomer glasses.

Samples prepared with bioglass and hydrated with various calcium chloride solutions exhibited ionic crosslinking when soaked for 24 hours in DI WATER.

Test Sample B was prepared similarly to Sample A, except the soaking solution following DHT was 1% Fe$_2$(SO$_4$)$_3$ in place of DI WATER.

Test Samples C and E were prepared with a slurry of glass, collagen, and DI WATER adjusted to a pH of 5. Sample C contained 90 wt % glass and Sample E contained 85 wt % glass. The slurries were then lyophilized and then subjected to DHT to form strips, soaked in DI WATER for 3 hours and lyophilized once more.

Test Sample D was prepared similarly to sample E except the slurry solution was pH adjusted CaCl$_2$ in place of DI WATER and HCl and the soaking solution was PBS in place of DI WATER.

Test Sample F was prepared by combining the glass and collagen, hydrating with DI WATER, and placing the sample into the tray. The tray was then soaked in DI WATER for 3 hours and lyophilized. Sample E did not undergo DHT.

A "plate" shape was used to evaluate the strips on the Shimadzu Mechanical Strength Tester. Tests were conducted under ambient conditions and all samples were tested in accordance with SOP PR-06.06 Mechanical Testing of CBG Product. Stress was applied in a circumferential direction. Specimens were elongated at a rate of 5 mm/min until failure, with the force and extension recorded over time.

The following table illustrates the composition and the tensile strength of the CBG Strip samples that were evaluated. Sample A is the control.

| | Composition | | | | | | | | Tensile |
|---|---|---|---|---|---|---|---|---|---|
| ID | Collagen % wt | 32-125 um % wt | 710-90 um % wt | 1-2 mm % wt | Slurry Prep | Lyo | DHT | Soaking Soln. | Strength (kPa) |
| A | 100 | 0 | 0 | 0 | RODI | Twice | Once | RODI | 4.24 |
| B | 100 | 0 | 0 | 0 | RODI | Twice | Once | 1% Fe$_2$(SO$_4$)$_3$ | 7.93 |
| C | 10 | 15 | 15 | 60 | RODI + HCl | Twice | Once | RODI | 14.37 |
| D | 15 | 12.5 | 12.5 | 60 | Ca(Cl)$_2$ pH 6.5 | Twice | Once | PBS | 14.87 |
| E | 15 | 12.5 | 12.5 | 60 | RODI + HCl | Twice | Once | RODI | 26.7 |
| F | 15 | 12.5 | 12.5 | 60 | RODI | Once | None | RODI | 28.93 |

EXPERIMENT 11

Preparation of CBG Strips

A "CBG strip" as defined herein is collagen and 45S5 bioactive glass that is lyophilized into a rectangular shape.

The control Sample A was prepared by making a slurry with collagen and DI WATER in a 1:1 ratio by weight. The slurry was then lyophilized and subjected to DHT in molds to form 5 cc strips. The collagen strips were then soaked in DI WATER for 3 hours and lyophilized once more.

The following bulk densities were obtained for CBG strips:

| Collagen Bioglass Ionically Crosslinked Composite (5 cc samples) | | |
|---|---|---|
| | Mass (g) | Bulk Density (g/cc) |
| 1 | 3.547 | 0.7094 |
| 2 | 3.582 | 0.7164 |
| 3 | 3.915 | 0.783 |
| 4 | 3.526 | 0.7052 |

-continued

Collagen Bioglass Ionically Crosslinked Composite (5 cc samples)

|  | Mass (g) | Bulk Density (g/cc) |
|---|---|---|
| 5 | 3.455 | 0.691 |
| 6 | 3.594 | 0.7188 |
| 7 | 3.856 | 0.7712 |
| Avg. | 3.639 | 0.7279 |
| Std. Dev. | 0.175 | 0.0350 |

% Porosity: 30-70%
Bulk Density: less than 1 g/cc

The control Sample A, was crosslinked using DHT processing. Therefore the increased tensile properties observed in the other Samples B through F can be attributed to ionic crosslinking. The tensile strength of Sample B when compared to the control indicates that ionic crosslinking occurred between the $Fe^{3+}_{(aq)}$ and the collagen fibers. Samples C and E exhibited higher tensile strengths than the control (Sample A). The compressive strength of Sample F indicates that CBG Strips can be crosslinked without DHT processing.

Samples prepared with bioglass exhibited greater tensile strength than the control that was only crosslinked with DHT. Sample F indicates that the collagen can be crosslinked and a high tensile strength can be achieved without DHT processing.

EXPERIMENT 12

Preparation of CBG Composite
Materials: collagen, Bioglass® (32-125 µm, 90-710 µm, and 1-2 mm), reverse osmosis deionized water, and 2N HCl.

A slurry was prepared by mixing 0.28 g of collagen with 4.55 mL reverse osmosis deionized water and 0.49 mL 2N HCl. The slurry was mixed until all collagen was saturated. Next, all glass starting with 1-2 mm (1.68 g), then 710-90 um (0.42 g), then 32-125 um (0.42 g) was poured into the beaker labeled "slurry" and the components mixed until homogenous.

The slurry was then lyophilized in molds to form 5 cc strips. The autoclaved molds were selected based on the desired amount of slurry to be placed in the mold and as per recommendations in the Table below (e.g., 2.5 cc mold for making 2.5 cc composites).

| Size of Well | Max Amount of Slurry Per Mold |
|---|---|
| 0.5 cc | 234 cc |
| 1 cc | 350 cc |
| 2.5 cc | 240 cc |
| 5 cc | 480 cc |
| 6 cc | 240 cc |
| 8 cc | 360 cc |
| 10 cc | 480 cc |

Following the lyophilization procedure, the molds were transferred into a clean room inside of a clean bag.
Next, molds were sealed, labeled and packaged.

EXPERIMENT 13

Fluid Absorption
The objective of the study was to determine the extent of fluid/blood absorption for the Bioactive Strip, MacroFORM Composite and Packable products. The study was conducted at ambient conditions: 68-74° F. and 40-60% relative humidity.

The following materials were used for the study: 5 cc Bioactive Strip, 2.5 cc MacroFORM Composite, and 5 cc MacroFORM Packable Morsels.

Dry weights were taken for each product. The devices were then hydrated with citrated sheep's blood and molded until the entirety of the product was saturated in blood. The hydrated weight was then taken of each sample and a measure of amount of blood absorbed per gram of product was calculated.

Figure 10:
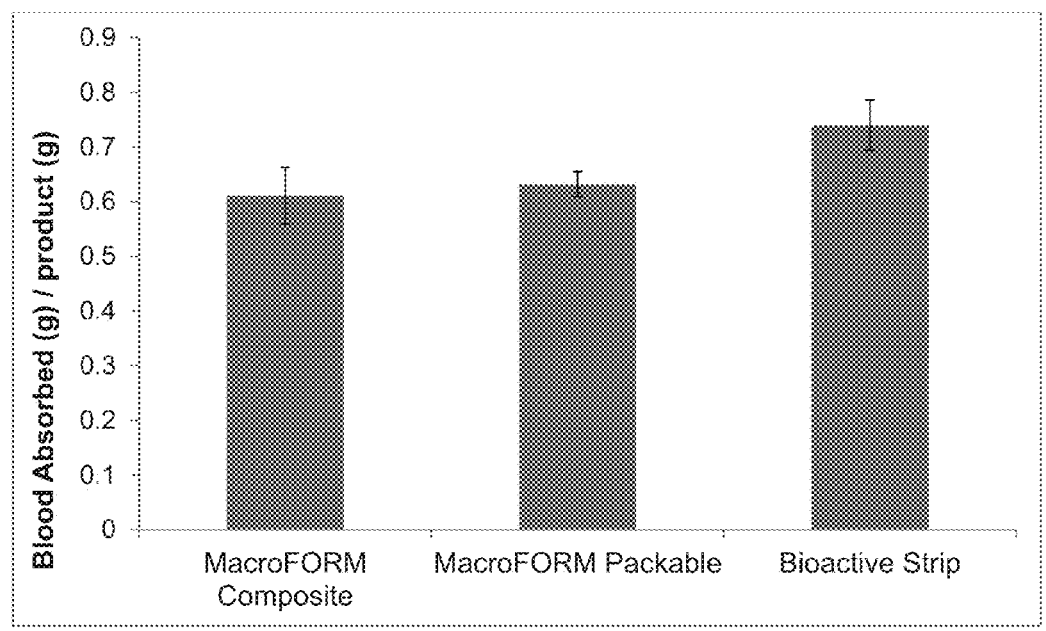
FIG. 10 depicts a graph of blood absorption of bioactive strip, composite and packable products.

The results of absorption test are show in the Table below and illustrated in FIG. 10.

TABLE

Average Blood Absorption

| SAMPLE | AVERAGE BLOOD ABSORBED PER GRAM OF PRODUCT (G) | STANDARD DEVIATION |
|---|---|---|
| 2.5 CC COMPOSITE | 0.611 | 0.052 |
| 5 CC PACKABLE GRAFT | 0.632 | 0.023 |
| 5 CC BIOACTIVE STRIP | 0.740 | 0.046 |

The MacroFORM products absorbed similar amounts of blood, approximately 0.6-0.75 grams of blood per gram of dry product.

EXPERIMENT 14

Porosity Study of CBG Composite
A porosity study was conducted in order to determine the porosity of the MacroFORM Composite.

Three samples of MacroFORM Composite from 3 separate lots (sample A, sample B and sample C).

Samples were evaluated using mercury porosimetry. The process measures porosity by applying pressure to a sample immersed in mercury. The pressure required to inject mercury into the sample is inversely proportional to the size of the pores (MPS). The applicable variables were dependent (percent porosity), independent (device) and lot number), Mercury parameters were as follows: Adv. Contact Angle: 130.000 degrees; Hg Surface Tension: 485.000 dynes/cm; Rec. Contact Angle: 130.000 degrees; and Hg Density: 13.5335 g/mL.

Samples were loaded into penetrometer. The penetrometer was sealed and placed in a low pressure port. The penetrometer's cup and stem were backfilled with mercury. Excess mercury was drained.

The test was completed after the porosity of the sample was determined.

The average percent porosity for the MacroFORM Composite batches were 79.3%±2.32 for lot 1104H5, 75.9%±1.12 for lot 1104N4, and 75.3%±0.83 for lot 1104M3. The Table below lists the porosity of each lot and the average and standard deviation of the MacroFORM Composite device.

TABLE

Porosity of MacroFORM Composite Lots

| Lot number | Sample | | | Average porosity (%) | Standard deviation |
|---|---|---|---|---|---|
| | A | B | C | | |
| | Porosity (%) | | | | |
| 1104H5 | 79.5453 | 81.4333 | 76.8174 | 79.2653 | 2.3207 |
| 1104N4 | 74.9383 | 75.7577 | 77.1489 | 75.9483 | 1.1176 |
| 1104M3 | 74.3159 | 75.8637 | 75.5929 | 75.2575 | 0.8266 |

Figure 11:
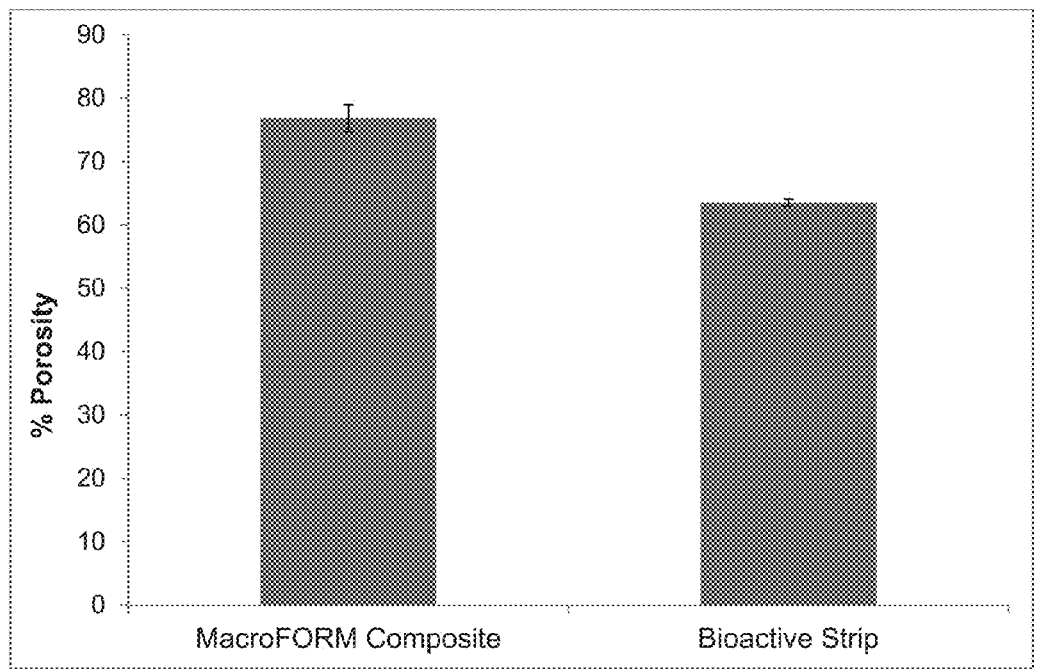
FIG. 11 depicts a bar graph showing the average porosity of MacroFORM Composite, and Bioactive Strip Lots.

The results are illustrated in FIG. 11.

The porosity measured in these devices facilitates the absorption of water or other fluids through capillary action.

EXPERIMENT 15

Porosity Study of Bioactive Strip

A study was conducted in order to determine the porosity of a Bioactive Strip. The testing was conducted by Micromeritics Pharmaceutical Services (MPS) in Norcross, Ga.

3 test samples from 3 separate lots were used in the study. Specifically, 3 NovaBone Bioactive Strip lots (1008P4, 1008P7, and 1008R1) were used. The tests protocols were developed and all testing was conducted by MPS (Norcross, Ga.).

Samples were evaluated using mercury porosimetry. The process measures porosity by applying pressure to a sample immersed in mercury. The pressure required to inject mercury into the sample is inversely proportional to the size of the pores (MPS).

Mercury Parameters included Adv. Contact Angle: 130.000 degrees; Hg Surface Tension: 485.000 dynes/cm; Rec. Contact Angle: 130.000 degrees; and Hg Density: 13.5335 g/mL.

Applicable variables included dependent (Pore Size Distribution and Percent Porosity), Independent (Device) and uncontrolled (shipping and storage conditions).

Samples were loaded into penetrometer. The penetrometer was sealed and placed in a low pressure port. The penetrometer's cup and stem were backfilled with mercury. The excess mercury was drained. The test was completed after the porosity of the sample was determined.

The Table below shows results of the porosity study of the Bioactive strips.

TABLE

Porosity of Bioactive Strip 1 Lots

| Lot number | Sample Number | | | Average porosity (%) | Standard deviation |
| | 1 | 2 | 3 | | |
| | Porosity (%) | | | | |
|---|---|---|---|---|---|
| 1008P4 | 63.1370 | 64.0095 | 61.8359 | 62.99 | 1.094 |
| 1008P7 | 64.1048 | 63.3744 | 64.6958 | 64.06 | 0.662 |
| 1008R1 | 61.9941 | 62.8057 | 65.4439 | 63.41 | 1.804 |

The average percent porosity for the Bioactive Strip batches were 63.0%±1.09 for 1008P4, 64.1%±0.66 for 1008P7, and 63.4%±1.80 for 1008R1. These results are illustrated in FIG. 11. There were no significant differences in percent porosity between Bioactive Strip Lots

EXPERIMENT 16

Tensile Strength Study of Bioactive Strip

A tensile strength study was conducted to test the resistance of the bioactive strip to a force tending to tear it apart, measured as the maximum tension the material can withstand without tearing.

Samples of bioactive strips were hydrated and soaked in reagent grade water before testing. The samples were then placed into the grips and tested at 5 mm/min until a 50% break was detected.

The tensile stress data for bioactive strip devices in provided in the Table below.

| Sample ID | Tensile stress (kPa) |
|---|---|
| JC-01-94-A | 60.1595 |
| JC-01-94-A-5 cc | 53.2472 |
| JC-01-94-A-5 cc | 32.8249 |
| JC-01-94-A-5 cc | 53.1097 |
| JC-01-94-A-5 cc | 40.5517 |
| Avg | 47.9786 |
| STDEV | 11.0369167 |

Figure 12A:
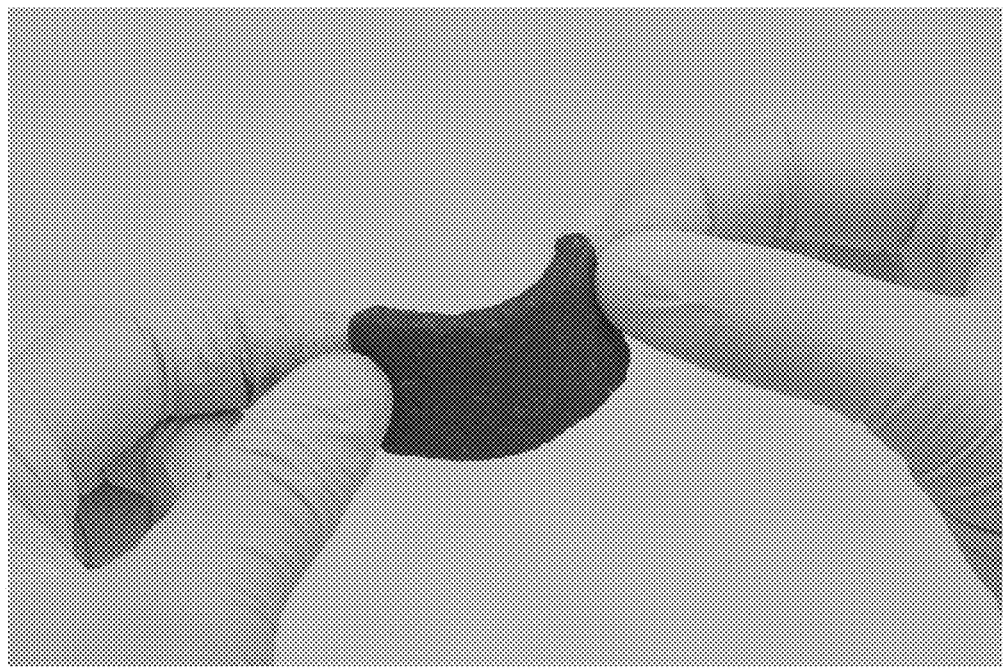
FIG. 12A is a photograph of the exemplary bioactive strip in a hydrated state.
Figure 12B:
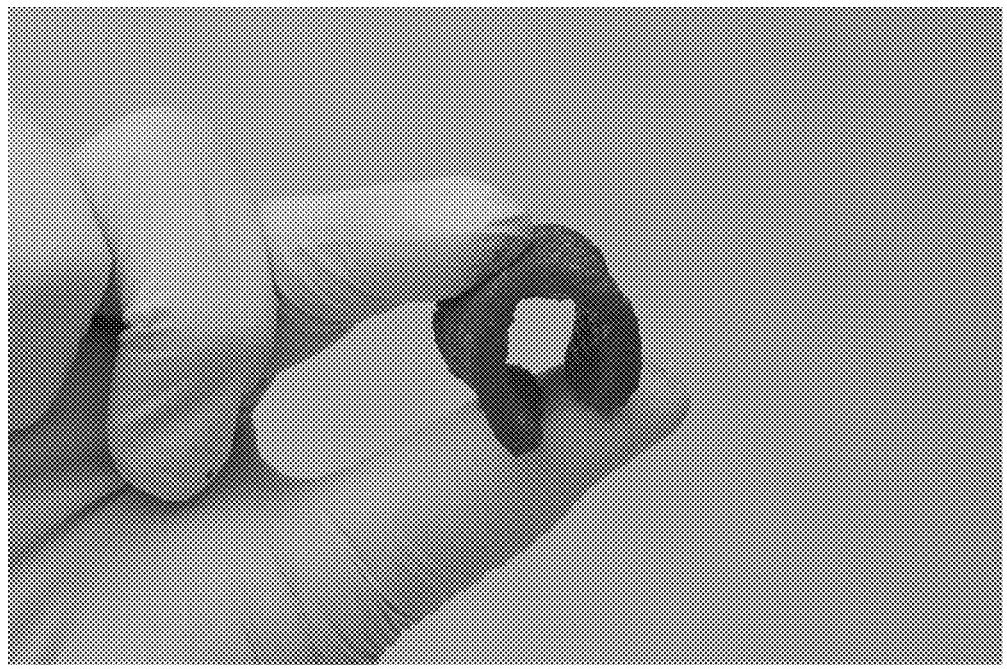
FIG. 12B is a photograph of the exemplary bioactive strip in a hydrated state.

The results show that the CBG material is a strong material and can withstand stress even though it is porous. In addition, the strip can bend and flex, as shown in FIGS. 12A and 12B.

Throughout this specification various indications have been given as preferred and alternative embodiments of the invention. However, the foregoing detailed description is to be regarded as illustrative rather than limiting and the invention is not limited to any one of the preferred embodiments. It should be understood that it is the appended claims, including all equivalents that are intended to define the spirit and scope of this invention.

The invention claimed is:

1. A kit for a minimally invasive delivery of a composition for regenerating bone at or near the site of a bony defect, the kit comprising:
   i. at least one tube comprising the composition for regenerating bone comprising about 2-60% collagen and about 40-98% bioactive glass, wherein the composition is free from calcium phosphate, and wherein the tube is capped or sealed when not in use;
   ii. a dispensing gun;
   iii. an adapter;
   iv. a plunger; and
   v. optionally, a dispensing tip.

2. The kit of claim 1, wherein the components of the kit are snap fit into a tray and a retainer is placed to maintain position of the components in the tray.

3. The kit of claim 2, wherein the tray holds up to four tubes comprising the composition.

4. The kit of claim 1, further comprising a syringe.

5. The kit of claim 1, further comprising a "Y" connector, tube connector, or an aspiration needle, or a combination thereof.

6. The kit of claim 1, wherein the bioactive glass has a porosity of up to 90%.

7. The kit of claim 1, wherein the bioactive glass has pores ranging from about 1 to about 5100 microns.

8. The kit of claim 1, wherein the bioactive glass has average pore size of <50 microns.

9. The kit of claim 1, wherein the bioactive glass has average pore size of 100 microns plus or minus 50 microns.

10. The kit of claim 1, wherein the bioactive glass has average pore size of 200 microns plus or minus 50 microns.

11. The kit of claim 1, wherein the bioactive glass has average pore size of 300 microns plus or minus 50 microns.

12. The kit of claim 1, wherein the bioactive glass has average pore size of 400 microns plus or minus 50 microns.

13. The kit of claim 1, wherein the bioactive glass has average pore size of 500 microns plus or minus 50 microns.

14. The kit of claim 1, wherein the bioactive glass has average pore size of 600 microns plus or minus 50 microns.

15. The kit of claim 1, wherein the bioactive glass has average pore size of 700 microns plus or minus 50 microns.

16. The kit of claim 1, wherein the composition comprises about 3-60% collagen and about 40-97% bioactive glass.

17. The kit of claim 1, wherein the composition comprises about 3-50% collagen and about 50-90% bioactive glass.

18. The kit of claim 1, wherein the composition further comprises an extracellular matrix molecule selected from the group consisting of integrins, fibronectin, vitronectin, osteopontin, bone sialoprotein thrombospondin, and fibrinogen, or a homo or copolymer of glycolides, acrylates, lactic acids, and caprolactone, and a combination thereof.

19. The kit of claim 1, wherein the composition is un-crosslinked.

20. The kit of claim 1, wherein the composition is crosslinked.

21. The kit of claim 1, wherein the composition is freeze-dried.

22. The kit of claim 1, wherein the bioactive glass have been pre-reacted in water, saline or a buffer.

23. The kit of claim 1, wherein the bioactive glass is not pre-reacted with a buffer.

24. The kit of claim 1, wherein the bioactive glass comprises 55-65% 1000-2000 um bioactive glass, 10-20% 90-710 um bioactive glass, and 10-20% 32-125 um bioactive glass.

25. The kit of claim 1, wherein the bioactive glass comprises 60% 1000-2000 um bioactive glass, 12.5% 90-710 um bioactive glass, and 12.5% 32-125 um bioactive glass.

26. The kit of claim 24, wherein the 1000-2000 um bioactive glass is porous.

27. The kit of claim 1, wherein the composition is in a form of a collagen bioactive glass composite.

28. The kit of claim 27, wherein the collagen bioactive glass composite is lyophilized.

29. The kit of claim 27, wherein the collagen and bioactive glass composite is lyophilized and crosslinked.

30. The kit of claim 1, wherein the composition is in a form of a mixture of:
   collagen in a granular, particulate, sphere or bead form, or a combination thereof, and
   bioactive glass in a granular, particulate, sphere or bead form, or a combination thereof.

31. The kit of claim 1, wherein the composition is in a granular, particulate, sphere or bead form, or a combination thereof, and comprises collagen and bioactive glass.

32. The kit of claim 1, wherein the composition further comprises at least one therapeutic agent, a signaling protein, glycosaminoglycan, or a combination thereof.

33. The kit of claim 1, wherein the bioactive glass is in a granular form, particulate form, matt form, fiber form, hemostatic sponge form, foam form, paste or putty form, or sphere or bead form, or a combination thereof.

34. The kit of claim 1, wherein the composition is pre-treated with water, saline, blood, bone marrow, a combination thereof, or other biocompatible substance to form a paste.

35. The kit of claim 1, wherein the bioactive glass comprises silicate based glasses.

36. The kit of claim 1, wherein the bioactive glass comprises borate based glasses.

37. A method for repairing or regenerating a bony defect comprising
   dispensing the composition for regenerating bone comprising about 2-60% collagen and about 40-98% bioactive glass at or near the site of the bony defect using the components of the kit of claim 1.

38. The method of claim 37, wherein the composition is moldable upon mixing with saline, blood, bone marrow, or other biocompatible fluid.

39. The method of claim 37, wherein the composition is pre-treated with water, saline, blood, bone marrow, a combination thereof, or other biocompatible substance to form a paste.

40. The method of claim 37, wherein the composition is in a form of a collagen bioactive glass composite.

41. The method of claim 40, wherein the collagen bioactive glass composite is lyophilized.

42. The method of claim 40, wherein the collagen and bioactive glass composite is lyophilized and crosslinked.

43. The method of claim 37, wherein the composition is in a form of a mixture of:
   collagen in a granular, particulate, sphere or bead form, or a combination thereof, and
   bioactive glass in a granular, particulate, sphere or bead form, or a combination thereof.

44. The method of claim 37, wherein the composition is in a granular, particulate, sphere or bead form, or a combination thereof, and comprises collagen and bioactive glass.

* * * * *